US008777856B2

(12) United States Patent
Stuebe et al.

(10) Patent No.: US 8,777,856 B2
(45) Date of Patent: Jul. 15, 2014

(54) DIAGNOSTIC SYSTEM AND METHOD FOR OBTAINING AN ULTRASOUND IMAGE FRAME

(75) Inventors: Susan Martignetti Stuebe, Whitefish Bay, WI (US); Daniel Lee Eisenhut, Hartland, WI (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 13/533,712

(22) Filed: Jun. 26, 2012

(65) Prior Publication Data

US 2013/0345563 A1 Dec. 26, 2013

(51) Int. Cl.
*A61B 8/00* (2006.01)

(52) U.S. Cl.
USPC .......................................... 600/437; 600/450

(58) Field of Classification Search
USPC .................................. 600/437–469
See application file for complete search history.

(56) References Cited

U.S. PATENT DOCUMENTS

| | | |
|---|---|---|
| 6,312,381 B1 | 11/2001 | Knell et al. |
| 2005/0033123 A1 | 2/2005 | Gardner et al. |
| 2005/0033179 A1 | 2/2005 | Gardner et al. |
| 2007/0016029 A1 | 1/2007 | Donaldson et al. |
| 2007/0055158 A1 | 3/2007 | Jackson et al. |
| 2008/0027319 A1* | 1/2008 | Gardner et al. ............... 600/437 |
| 2009/0099449 A1 | 4/2009 | Lundberg |
| 2009/0180675 A1 | 7/2009 | Li et al. |
| 2009/0198134 A1* | 8/2009 | Hashimoto et al. ........... 600/443 |
| 2009/0247872 A1 | 10/2009 | Rowlandson et al. |
| 2010/0036247 A1* | 2/2010 | Yamamoto et al. ........... 600/443 |
| 2010/0168578 A1 | 7/2010 | Garson, Jr. et al. |
| 2010/0195881 A1 | 8/2010 | Orderud et al. |
| 2010/0228127 A1* | 9/2010 | Allain et al. ................... 600/443 |
| 2011/0077516 A1 | 3/2011 | Abe |
| 2012/0065510 A1 | 3/2012 | Snare et al. |
| 2012/0310088 A1 | 12/2012 | Noguchi et al. |
| 2013/0281854 A1 | 10/2013 | Stuebe et al. |

FOREIGN PATENT DOCUMENTS

EP 1559373 A1 8/2005

OTHER PUBLICATIONS

V. Palmieri, et al. Reliability of Echocardiographic Assessment of Left Ventricular Structure and Function; Journal of the American College of Cardiology;1999, vol. 34 No. 5.
Search Report and Written Opinion from GB Application No. 1311305.5 dated Jan. 9, 2014.

* cited by examiner

*Primary Examiner* — Sanjay Cattungal
(74) *Attorney, Agent, or Firm* — The Small Patent Law Group; Dean D. Small

(57) ABSTRACT

An ultrasound diagnostic system is provided that includes an ultrasound imaging device having an ultrasound probe that is configured to provide an ultrasound image of the heart during an ultrasound imaging session. The diagnostic system also includes a user interface including an operator display that is configured to concurrently display a reference image frame and the ultrasound image of the ultrasound imaging session. The user interface is configured to receive operator inputs to adjust a view of the heart in the ultrasound image and acquire a set of image frames of the heart. The diagnostic system also includes a cardiac analyzer that is configured to automatically identify a measurement frame from the set of image frames. The measurement frame includes the heart at a designated orientation and at a designated cardiac condition.

20 Claims, 10 Drawing Sheets

DIAGNOSTIC SYSTEM AND METHOD FOR OBTAINING AN ULTRASOUND IMAGE FRAME

BACKGROUND OF THE INVENTION

The subject matter herein relates generally to ultrasound systems and methods for obtaining data relating to a patient's health and/or anatomy, and more particularly, to ultrasound systems and methods that are configured to obtain dimensional and/or functional data of an anatomical structure.

Healthcare providers may use various types of systems to diagnose medical conditions. For instance, doctors or other qualified individuals may use an ultrasound imaging system to obtain ultrasound images of the heart. Ultrasound images of the heart (also called echocardiograms or "echos") may show anatomical structures (e.g., ventricles, atria, valves, septum, and the like) as well as blood flow through the heart. An ultrasound image of the heart may be used to measure dimensions of designated structures of the heart to diagnose a medical condition.

In some cases, it may be informative to obtain ultrasound images of an anatomical structure from different time periods and compare the ultrasound images. For instance, an echocardiogram of a patient's heart after treatment may be compared to a baseline ultrasound image that was obtained before treatment. Such comparison may assist in determining whether and to what extent the patient is responding to treatment. As a specific example, cardiovascular mortality and morbidity increases with increasing values of left ventricular (LV) mass. Left-ventricular hypertrophy (LVH) is a thickening of the myocardium of the left ventricle that is also associated with cardiovascular mortality and morbidity. After obtaining ultrasound images from different time periods, a measurement of the myocardium obtained before treatment can be compared to a measurement of the myocardium obtained after treatment to determine whether the LV mass or LVH has reduced.

However, the value of the comparison may be adversely affected if the different ultrasound images show views of the heart that are not sufficiently comparable. Accordingly, a doctor's diagnosis may be inaccurate and/or the subsequent decisions regarding treatment of the patient may be affected.

BRIEF DESCRIPTION OF THE INVENTION

In one embodiment, an ultrasound diagnostic system is provided that includes a storage system configured to store a reference image frame of a heart. The reference image frame is acquired during a first ultrasound imaging session. The reference image frame includes the heart at a corresponding orientation and at a corresponding cardiac condition. The diagnostic system also includes an ultrasound imaging device having an ultrasound probe that is configured to provide an ultrasound image of the heart during a second ultrasound imaging session. The diagnostic system also includes a user interface including an operator display that is configured to concurrently display the reference image frame and the ultrasound image of the second ultrasound imaging session. The user interface is configured to receive operator inputs to adjust a view of the heart in the second ultrasound image and acquire a set of image frames of the heart. The diagnostic system also includes a cardiac analyzer that is configured to automatically identify a measurement frame from the set of image frames. The measurement frame includes the heart at a designated orientation that is similar to the corresponding orientation of the reference image frame and includes the heart at a designated cardiac condition that is similar to the cardiac condition of the reference image frame.

In another embodiment, an ultrasound diagnostic is provided that includes a storage system configured to store a previously-acquired reference image of a heart. The reference image is from a first ultrasound imaging session and includes the heart at a corresponding orientation. The diagnostic system also includes an ultrasound imaging device having an ultrasound probe that is configured to acquire a real-time image of the heart during a second ultrasound imaging session. The probe is configured to be controlled by an operator to change a view of the heart. The diagnostic system also includes a user interface having an operator display that is configured to concurrently display to the operator the reference and real-time images during the second imaging session. The user interface is configured to receive operator inputs to acquire a cardiac-cycle image of the heart from the real-time image. The diagnostic system also includes a cardiac analyzer that is configured to automatically identify a measurement frame from the cardiac-cycle image. The measurement frame includes the heart at a designated orientation that is similar to the corresponding orientation of the reference image frame and includes the heart at a designated cardiac condition.

In another embodiment, a method of obtaining ultrasound images of a heart is provided. The method includes displaying a reference image acquired from a first ultrasound imaging session. The reference image includes the heart at a corresponding orientation. The reference image is displayed during a second ultrasound imaging session that occurs after the first ultrasound imaging session. The method also includes displaying a real-time image of the heart that is obtained by an ultrasound probe during the second imaging session. The real-time image and the reference image are displayed concurrently to an operator. The method also includes adjusting a view of the heart in the real-time image and acquiring a cardiac-cycle image of the heart from the real-time image. The cardiac-cycle image includes the heart at a designated orientation that is similar to the corresponding orientation of the heart in the reference image. The method also includes automatically identifying a measurement frame from the cardiac-cycle image. The measurement frame includes the heart at the designated orientation and includes the heart at a designated cardiac condition.

DETAILED DESCRIPTION OF THE INVENTION

Figure 1:
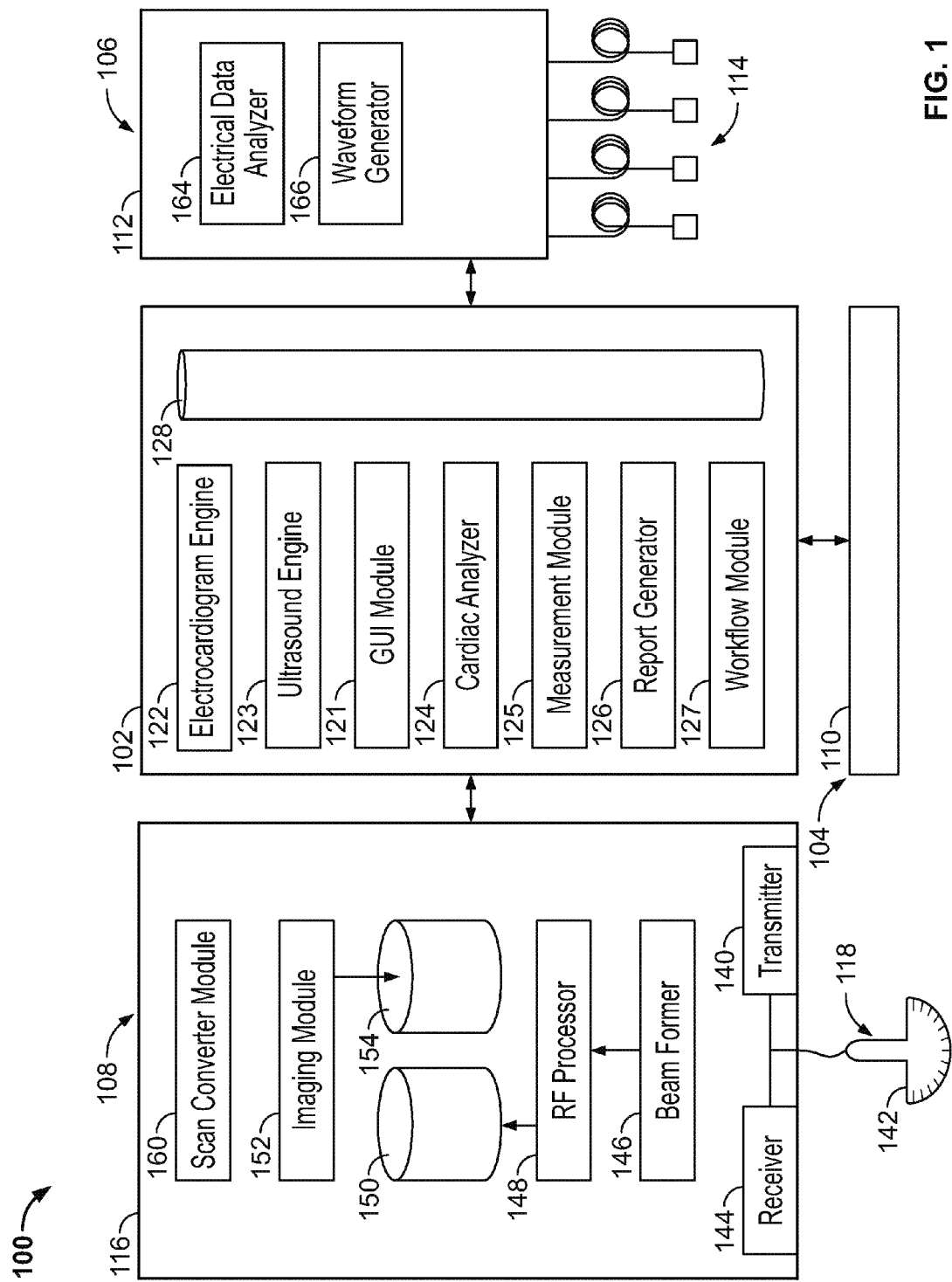
FIG. 1 is a block diagram of a diagnostic ultrasound system formed in accordance with one embodiment for obtaining an ultrasound image.

Exemplary embodiments that are described in detail below provide systems and methods for obtaining a diagnostic medical image, such as an ultrasound image. Optionally, embodiments may also be used in obtaining an electrocardiogram (ECG) in addition to the image. Embodiments described herein may include systems and methods for obtaining data relating to a heart that may be used to diagnose a medical condition of the heart. For example, one or more embodiments may be used to determine dimensions of anatomical structures of the heart. An exemplary medical condition that one or more embodiments may be used to diagnose is left-ventricular hypertrophy (LVH). Embodiments may also be used to provide information to a qualified doctor or other individual that may assist the doctor in diagnosing hypertension in a patient. However, embodiments described herein may assist in diagnosing other medical conditions.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

FIG. 1 is a block diagram of a medical diagnostic system 100 formed in accordance with one embodiment for obtaining an ultrasound image and, optionally, an electrocardiogram (ECG). The diagnostic system 100 includes a computing system 102, a user interface 104, an electrocardiogram (ECG) monitor or device 106, and an ultrasound imaging device 108. The computing system 102 is communicatively coupled to the user interface 104 and the ECG and imaging devices 106, 108 and is configured to control operation of the user interface 104 and the ECG and imaging devices 106, 108. The computing system 102 may also generate reports and/or provide at least some analysis of the imaging and electrical data obtained. In one embodiment, the ECG and imaging devices 106, 108 form sub-systems of the diagnostic system 100.

In an exemplary embodiment, the computing system 102 includes one or more processors/modules configured to instruct the user interface 104 and the ECG and imaging devices 106, 108 to operate in a designated manner during, for example, a diagnostic session. The computing system 102 is configured to execute a set of instructions that are stored in one or more storage elements (e.g., instructions stored on a tangible and/or non-transitory computer readable storage medium) to control operation of the diagnostic system 100. The set of instructions may include various commands that instruct the computing system 102 as a processing machine to perform specific operations such as the workflows, processes, and methods described herein. In FIG. 1, the computing system 102 is indicated as a separate unit with respect to the user interface 104 and the ECG and imaging devices 106, 108. However, it is understood that computing system 102 is not necessarily separate from the user interface 104 and the ECG and imaging devices 106, 108. Instead, the computing system 102 may be distributed in parts of the user interface 104 and/or the ECG and imaging devices 106, 108.

The user interface 104 may include hardware, firmware, software, or a combination thereof that enables an individual (e.g., an operator) to directly or indirectly control operation of the diagnostic system 100 and the various components thereof. As shown, the user interface 104 includes an operator display 110. The operator display 110 may be multiple separate displays that are oriented to be viewed by the operator. In some embodiments, the user interface 104 may also include one or more input devices (not shown), such as a physical keyboard, mouse, and/or touchpad. In an exemplary embodiment, the operator display 110 is a touch-sensitive display (e.g., touchscreen) that can detect a presence of a touch from an operator of the diagnostic system 100 and can also identify a location in the display area of the touch. The touch may be applied by, for example, at least one of an individual's hand, glove, stylus, or the like. As such, the touch-sensitive display may receive inputs from the operator and also communicate information to the operator.

The ECG device 106 includes a base unit 112 and a plurality of electrodes 114 (or leads) that are communicatively coupled to the base unit 112. The imaging device 108 includes a base unit 116 and an ultrasound probe or transducer 118. The computing system 102, the user interface 104, the ECG and imaging devices 106, 108 may be constructed into a single device or apparatus. For example, the computing system 102, the user interface 104, and the base units 112, 116 may be integrated into one component that is communicatively coupled to the probe 118 and the electrodes 114. For example, the integrated component may be similar to a tablet computer, a laptop computer, or desktop computer. Alternatively, the diagnostic system 100 may be several components that may or may not be located near each other. In some embodiments, the base units 112, 116 share a common housing as shown in the portable diagnostic system 600 shown in FIG. 10.

As used herein, an "anatomical structure" may be an entire organ or system or may be an identifiable region or structure within the organ or system. In particular embodiments, the anatomical structures that are analyzed are structures of the heart. Examples of anatomical structures of the heart include, but are not limited to, the epicardium, endocardium, midmyocardium, one or both atria, one or both ventricles, walls of the atria or ventricles, valves, a group of cardiac cells within a predetermined region of the heart, and the like. In particular embodiments, the anatomical structures include the septal and posterior walls of the left ventricle. However, in other embodiments, anatomical structures may be structures found elsewhere in the body of the patient, such as other muscles or muscle systems, the nervous system or identifiable nerves within the nervous system, organs, and the like. It should also be noted that although the various embodiments may be described in connection with obtaining data related to a patient that is human, the patient may also be an animal.

In one or more embodiments, "communicatively coupled" includes devices or components being electrically coupled to each other through, for example, wires or cables and also includes devices or components being wirelessly connected to each other such that one or more of the devices or components of the diagnostic system 100 may be located remote from the others. For example, the user interface 104 may be located at one location (e.g., hospital room or research laboratory) and the computing system 102 (or portions thereof) may be remotely located (e.g., central server system).

In one or more embodiments, a "diagnostic session," which in particular embodiments may be called an "ultrasound imaging session," is a period of time in which an operator uses the diagnostic system 100 to prepare for and/or obtain data from a patient that may be used to diagnose a medical condition. During a diagnostic session, the operator may use at least one of the user interface 104 to enter patient information, the ECG device 106, the imaging device 108, or other biomedical device. By way of example, a diagnostic session may include at least one of coupling the electrodes 114 to a patient's body, applying gel to the patient's body for ultrasound imaging, capturing ultrasound images using the probe 118, and interacting with the user interface 104 to obtain the diagnostic data of the patient. In some embodiments, the diagnostic system 100 is configured to acquire similar data during first and second diagnostic sessions that are separated by a period of time. The period of time may be, for example, a time period in which therapy (e.g., at least one of surgery, medication, change in diet, or exercise) may have a measurable effect on the anatomical structure. The time period may be measured in seconds, minutes, days, weeks, months, and years. As one specific example, the first and second diagnostic sessions may be first and second ultrasound imaging sessions of the heart to determine if therapy has changed (e.g., reduced) the size of one or more structures of the heart.

The diagnostic data may include at least one of an ultrasound image, an ECG recording (or reading), or a measurement derived from the ECG recording and/or ultrasound image. The ultrasound image may include a view of the heart when the heart is in a designated orientation with respect to the ultrasound probe and at a designated contractive condition. When the heart is in the designated orientation, one or more structural measurements of the heart may be determined from the corresponding ultrasound image. The structural measurements determined may include dimensions (e.g., thickness), volume, area, and the like. Other measurements may be computed from the structural measurements that are obtained from the ultrasound image(s).

In one or more embodiments, a diagnostic ultrasound image includes an imaging obtained through an ultrasound imaging system that is based on one or more ultrasound processing techniques (e.g., color-flow, acoustic radiation force imaging (ARFI), B-mode imaging, spectral Doppler, acoustic streaming, tissue Doppler, C-scan, elastography, M-mode, power Doppler, harmonic tissue strain imaging, among others). The ultrasound images may be two-dimensional (2D), three-dimensional (3D), or four-dimensional (4D). An ultrasound image may include only a single image frame or may include a set of image frames. The set of image frames may be a series of image frames obtained over a duration of time. The duration of time may encompass one or more cardiac cycles. In order to distinguish different images or image frames, an ultrasound image (or an image frame) may also be referred to as a reference image (or reference frame), a real-time image (or a real-time frame), a cardiac-cycle image (or a cardiac-cycle frame).

In one or more embodiments, a "predetermined or designated cardiac-cycle event" may be an identifiable stage or moment in the cardiac cycle. In some cases, the stage or moment may occur when various structures of the heart have a relative position with respect to each other. For example, the stage or moment may occur when two walls have a greatest separation distance therebetween or a least separation distance therebetween (e.g., when a portion of the heart is contracted). This may also be characterized as a contractive condition of the heart. As another example, the stage or moment may occur when a valve is fully opened or closed. The predetermined cardiac-cycle event may also be determined by analyzing the electrical activity of the heart (e.g., the ECG). In particular embodiments, the predetermined cardiac-cycle event is an end diastole of the cardiac cycle.

In one or more embodiments, a "user-selectable element" includes an identifiable element that is configured to be activated by an operator. The user-selectable element may be a physical element of an input device, such as a keyboard or keypad, or the user-selectable element may be a graphical-user-interface (GUI) element (e.g., a virtual element) that is displayed on a screen. User-selectable elements are configured to be activated by an operator during a diagnostic session. Activation of the user-selectable element may be accomplished in various manners. For example, the user-selectable element (physical or virtual) may be pressed by the operator, selected using a cursor and/or a mouse, selected using keys of a keyboard, voice-activated, and the like. By way of example, the user-selectable element may be a key of a keyboard (physical or virtual), a tab, a switch, a lever, a drop-down menu that provides a list of selections, a graphical icon, and the like. In some embodiments, the user-selectable element is labeled or otherwise differentiated (e.g., by drawing or unique shape) with respect to other user-selectable elements. When a user-selectable element is activated by an operator, signals are communicated to the diagnostic system 100 (e.g., the computing system 102) that indicate the operator has selected and activated the user-selectable element and, as such, desires a predetermined action. The signals may instruct the diagnostic system 100 to act or respond in a predetermined manner.

In some embodiments, the diagnostic system 100 may be activated by user motions without specifically engaging a user-selectable element. For example, the operator of the diagnostic system 100 may engage the screen by quickly tapping, pressing for longer periods of time, swiping with one or more fingers (or stylus unit), or pinching the screen with multiple fingers (or styluses). Other gestures may be recognized by the screen. In other embodiments, the gestures may be identified by the diagnostic system 100 without engaging the screen. For example, the diagnostic system 100 may include a camera (not shown) that monitors the operator. The diagnostic system 100 may be programmed to respond when the operator performs predetermined motions.

The imaging device 108 includes a transmitter 140 that drives an array of transducer elements 142 (e.g., piezoelectric crystals) within the probe 118 to emit pulsed ultrasonic signals into a body or volume. The pulsed ultrasonic signals may be for imaging of a ROI that includes an anatomical structure, such as a heart. The ultrasonic signals are back-scattered from structures in the body, for example, adipose tissue, muscular tissue, blood cells, veins or objects within the body (e.g., a catheter or needle) to produce echoes that return to the transducer elements 142. The echoes are received by a receiver 144. The received echoes may be provided to a beamformer 146 that performs beamforming and outputs an RF signal. The RF signal may then be provided to an RF processor 148 that processes the RF signal. Alternatively, the RF processor 148 may include a complex demodulator (not shown) that demodulates the RF signal to form IQ data pairs representative of the echo signals. The RF or IQ signal data may then be provided directly to a memory 150 for storage (e.g., temporary storage).

The imaging device 108 may also include a processor or imaging module 152 to process the acquired ultrasound information (e.g., RF signal data or IQ data pairs) and prepare frames of ultrasound information for display. The imaging module 152 is adapted to perform one or more processing operations according to a plurality of selectable ultrasound modalities on the acquired ultrasound information. Acquired ultrasound information may be processed in real-time during a diagnostic session as the echo signals are received. Additionally or alternatively, the ultrasound information may be stored temporarily in the memory 150 during a diagnostic session and processed in less than real-time in a live or off-line operation. An image memory 154 is included for storing processed frames of acquired ultrasound information that are not scheduled to be displayed immediately. The image memory 154 may comprise any known data storage medium, for example, a permanent storage medium, removable storage medium, etc.

The imaging module 152 is communicatively coupled to the user interface 104 that is configured to receive inputs from the operator to control operation of the imaging device 108. The display 110 may automatically display, for example, a 2D, 3D, or 4D ultrasound data set stored in the memory 150 or 154 or currently being acquired. The data set may also be displayed with a graphical representation (e.g., a reference object). One or both of the memory 150 and the memory 154 may store 3D data sets of the ultrasound data, where such 3D data sets are accessed to present 2D and 3D images. For example, a 3D ultrasound data set may be mapped into the corresponding memory 150 or 154, as well as one or more reference planes. The processing of the data, including the data sets, may be based in part on operator inputs, for example, user selections received at the user interface 104.

In some embodiments, the ultrasound data may constitute IQ data pairs that represent the real and imaginary components associated with each data sample. The IQ data pairs may be provided to one or more image-processing modules (not shown) of the imaging module 152, for example, a color-flow module, an acoustic radiation force imaging (ARFI) module, a B-mode module, a spectral Doppler module, an acoustic streaming module, a tissue Doppler module, a C-scan module, and an elastography module. Other modules may be included, such as an M-mode module, power Doppler module, harmonic tissue strain imaging, among others. However, embodiments described herein are not limited to processing IQ data pairs. For example, processing may be done with RF data and/or using other methods.

Each of the image-processing modules may be configured to process the IQ data pairs in a corresponding manner to generate color-flow data, ARFI data, B-mode data, spectral Doppler data, acoustic streaming data, tissue Doppler data, C-scan data, elastography data, among others, all of which may be stored in a memory temporarily before subsequent processing. The image data may be stored, for example, as sets of vector data values, where each set defines an individual ultrasound image frame. The vector data values are generally organized based on the polar coordinate system. A scan converter module 160 may access and obtain from the memory the image data associated with an image frame and convert the image data to Cartesian coordinates to generate an ultrasound image formatted for display.

The ECG device 106 may include an electrical data analyzer 164 and a waveform generator 166. The data analyzer 164 may be configured to analyze the electrical signals detected by the electrodes 114 and verify that the electrical signals from each electrode 114 are accurate for the location of the corresponding electrode 114. More specifically, the data analyzer 164 may facilitate determining if the electrodes are (a) not sufficiently coupled to the patient; (b) improperly located on the patient; and/or (c) are faulty. The waveform generator 166 is configured to receive the electrical signals from the electrodes 114 and process the collective signals into waveform data. The waveform data may be received by the user interface 104 and displayed to the operator as, for example, a PQRST waveform. The waveform data and/or the presentation of the waveform may be based, at least in part, on operator selections.

The computing system 102 includes a plurality of modules or sub-modules that control operation of the diagnostic system 100. For example, the computing system 102 may include the modules 121-127 and a storage system 128 that communicates with at least some of the modules 121-127 and the ECG and imaging devices 106, 108. The graphical user interface (GUI) module 121 may coordinate with the other modules and the ECG and imaging devices 106, 108 for displaying various objects in the display 110. For example, various images of the user-selectable elements, described in greater detail below, may be stored in the storage system 128 and provided to the display 110 by the GUI module 121.

The computing system 102 also includes a workflow module 127. The workflow module 127 may be configured to respond to operator inputs during a workflow of the diagnostic system 100 and instruct the user interface 104 to show different screens to the operator on the display 110. The screens may be shown in a predetermined manner to guide the operator during the workflow. More specifically, the workflow module 127 may command the user interface to show at least some of the screens in a designated order. As one example, during a stage of the workflow (described in greater detail below), the user interface 104 may show different screens to guide the operator to locate a reference object with respect to an ultrasound image of the heart. When the operator activates, for example, "NEXT" or "SAVE" user-selectable elements on a first screen, the workflow module 127 may instruct the user interface to show a predetermined second screen that is configured to follow the first screen in the workflow.

The computing system 102 may include an ECG engine 122 configured to communicate with and control operation of the ECG device 106. The computing system 102 may also include an ultrasound engine 123 that may be configured to control operation of the imaging device 108. The ECG and ultrasound engines 122, 123 may receive operator inputs and communicate the operator inputs to the probe 118 and the ECG device 106.

The computing system 102 may also include a cardiac analyzer 124 that is configured to analyze ultrasound data. The ultrasound data may be obtained by the imaging device 108 or the ultrasound data may be provided by another source (e.g., database). The cardiac analyzer 124 may analyze ultrasound images and automatically identify a designated ultrasound image (also called cardiac-cycle image) from a set of ultrasound images based on the ultrasound data. The cardiac-cycle image may include the heart at a predetermined cardiac-cycle event.

A measurement module 125 of the computing system 102 may be configured to analyze the cardiac-cycle image and automatically position a reference object relative to the heart in the cardiac-cycle image. The reference object may assist in acquiring measurements of the heart. In the illustrated embodiment, the reference object is a projection line. However, in other embodiments, the reference object may be any shape that facilitates acquiring measurements from the ultrasound images.

The computing system 102 may also include a report generator 126. The report generator 126 may analyze measurements obtained by the ECG device 106 and/or the imaging device 108 and provide a report that may assist a doctor or otherwise qualified individual in diagnosing a medical condition. As such, the report generator 126 may also be referred to as a diagnostic module. The measurements analyzed by the report generator 126 may include an ECG recording, ultrasound images, measurements of the heart in at least one of the ultrasound images, and other patient information. In some embodiments, the report generator 126 does not process or analyze the measurements, but simply generates a report that includes the measurements in a predetermined format. In some embodiments, the report is a virtual report stored in the diagnostic system 100.

Figure 2:
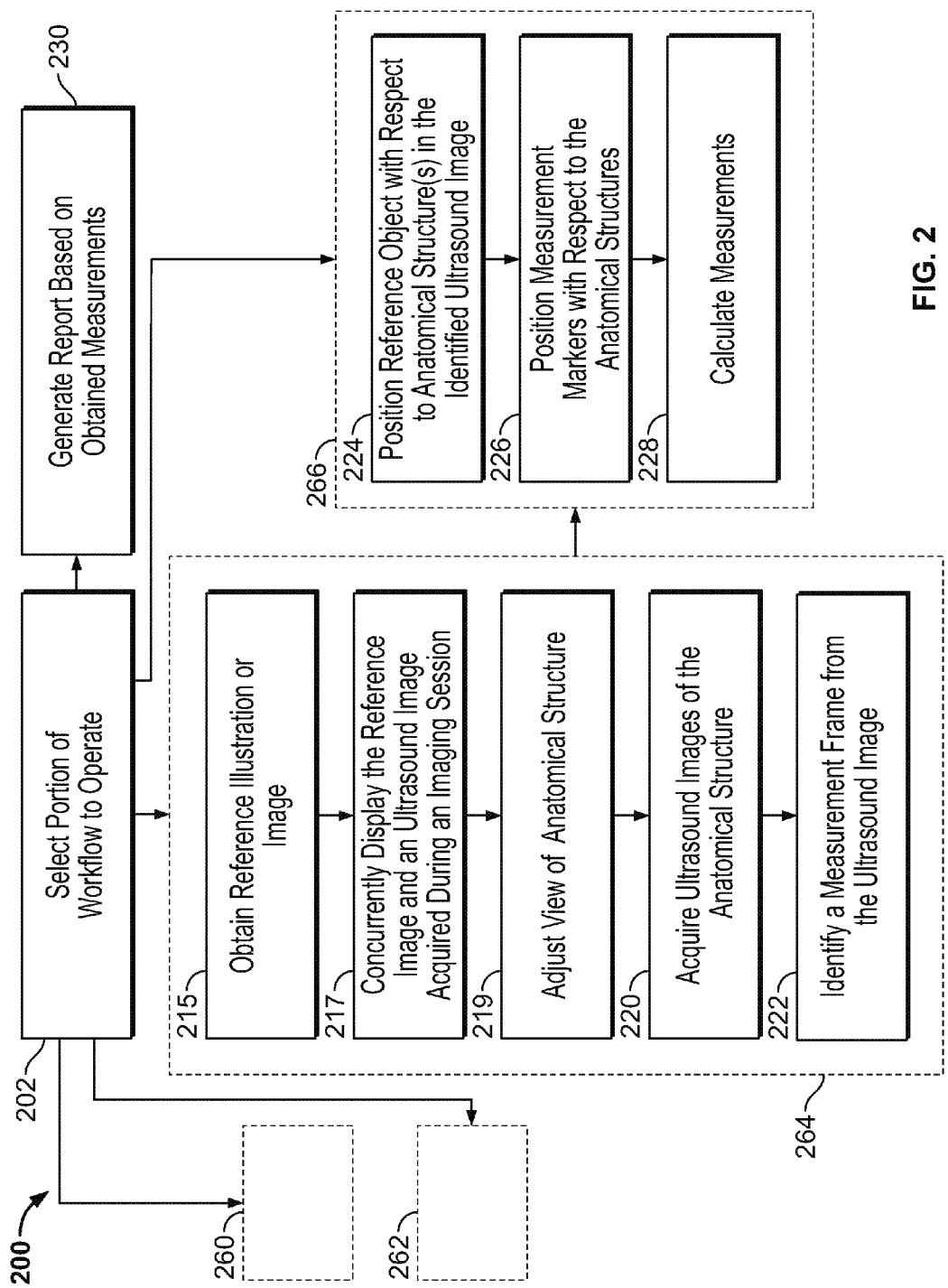
FIG. 2 is a flow chart that illustrates a workflow in accordance with one embodiment that may be performed with the diagnostic ultrasound system of FIG. 1.

FIG. 2 is a flowchart illustrating a workflow or method 200 in accordance with one embodiment that may be referred to throughout the description of FIGS. 3-8. Although the workflow 200 shows numerous operations or steps that an operator may perform using a diagnostic system, embodiments described herein are not limited to performing each and every operation described herein and/or performing operations in the order shown in FIG. 2. Embodiments may also include operations that are not shown in FIG. 2, but are described elsewhere herein. Embodiments described herein are not limited to the order shown in FIG. 2 unless explicitly stated otherwise.

FIGS. 3-8 shows various display screens or windows that may be displayed to an operator by one or more embodiments. The workflow 200 may include an administrative stage 260 and a plurality of data-acquisition stages that, in the illustrated embodiment, include an ECG-acquisition stage 262, an ultrasound-acquisition stage 264, a measurement stage 266, and a workflow-generation stage 230. The workflow 200 may include selecting at 202 a portion of the workflow to operate. The administrative and ECG-acquisition stages 260, 262 may be performed, for example, as described in U.S. application Ser. No. 13/454,945, filed on Apr. 24, 2012, which is incorporated by reference in its entirety for all purposes. The different stages may be activated by selecting one of a plurality of tabs 321-326, which include a PATIENT tab 321, an ECG tab 322, an ULTRASOUND tab 323, a REPORT tab 324, a MGMT tab 325, and a CONFIG tab 326.

Figure 3:
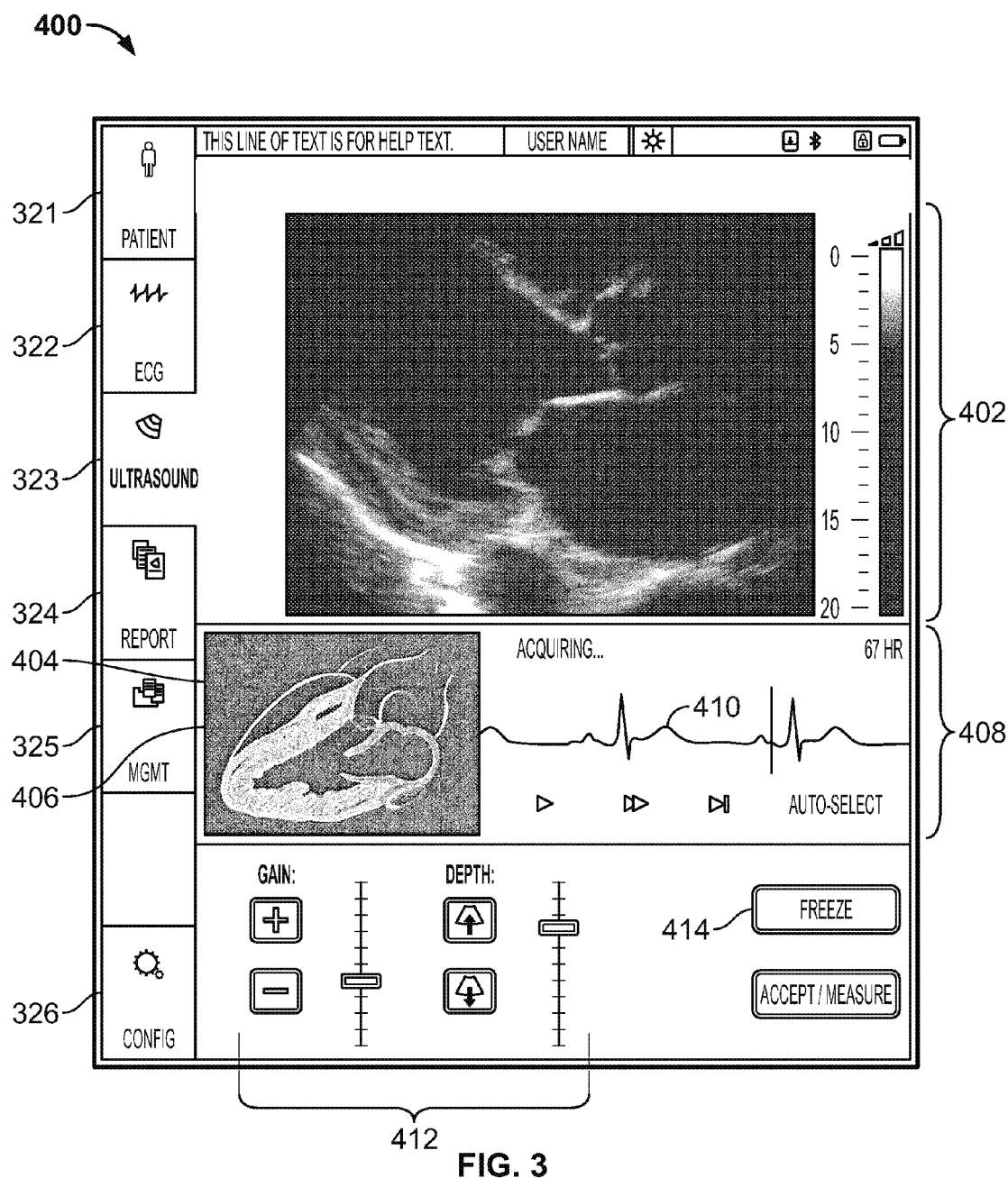
FIG. 3 shows an ultrasound-acquisition screen that may be displayed by the diagnostic ultrasound system of FIG. 1.

FIG. 3 shows an ultrasound-acquisition screen 400 that may be displayed to the operator when the ULTRASOUND tab 323 is activated (e.g., during the ultrasound-acquisition stage 264). During the ultrasound-acquisition stage 264, one or more ultrasound images may be acquired using, for example, the diagnostic system 100. The ultrasound-acquisition screen 400 includes an image portion 402 where an ultrasound image is displayed and a reference advisor 404 where a reference illustration 406 of an anatomical structure (e.g., heart) is displayed. A reference illustration is a drawing or diagram that includes a representation of the anatomical structure. The reference illustration is not a diagnostic ultrasound image (e.g., B-mode image). In alternative embodiments, a previously-acquired diagnostic ultrasound image 407 (shown in FIG. 8) may be displayed in the reference advisor 404. The ultrasound-acquisition screen 400 may also include a waveform portion 408 in which a signal waveform 410 is displayed, wherein the signal waveform 410 is associated with the reference illustration 406 or the previously-acquired image 407, and operator controls 412.

In an exemplary embodiment, the ultrasound images are B-mode images. However, other ultrasound images may be used based on various ultrasound imaging modalities, such as those described herein. The operator controls 412 may enable the operator to change different acquisition settings or parameters, such as the gain of the ultrasound images and the depth of the ultrasound images shown in FIG. 3. The signal waveform 410 may be obtained by a single ECG electrode that is coupled to the body of the patient. In alternative embodiments, the signal waveform may be obtained by multiple electrodes.

The workflow 200 may also include obtaining at 215 a reference illustration or reference image. The reference illustration or reference image may show a designated orientation of an anatomical structure (e.g., heart) at a desired cardiac-cycle event. The reference image may be previously acquired from a first imaging session. The reference image is a diagnostic medical image (e.g., diagnostic ultrasound image) that may be from the patient-of-interest or another patient (e.g., the reference image may be an atlas image). The reference illustration or image may be automatically obtained or the operator may enter inputs to retrieve the desired reference illustration or image. The workflow 200 may also include concurrently displaying the reference illustration or image with an ultrasound image during a second imaging session. For example, the reference image from the first imaging session may be concurrently displayed with the ultrasound images of the second imaging session. When the images are concurrently displayed, the reference image is displayed at least a portion of the time the ultrasound image(s) is displayed.

In FIG. 3, the ultrasound-acquisition screen 400 is showing the reference illustration 406. However, in other embodiments, the previously-acquired diagnostic ultrasound image 407 (FIG. 8) may be shown to the operator. The object of the ultrasound image (e.g., the heart) may have a designated orientation and be in a predetermined cardiac-cycle event for obtaining measurements. In particular embodiments, the desired orientation of the heart is a parasternal long-axis view of the left ventricle. As such, the reference illustration 406 or the reference image 407 may show the parasternal long-axis view of the left ventricle. In particular embodiments, the predetermined cardiac-cycle event is the end diastole of the cardiac cycle.

The workflow 200 may also include adjusting at 219 a view of the anatomical structure to obtain an ultrasound image of the anatomical structure at a desired orientation and/or moment in time. For example, in embodiments where the anatomical structure is the heart, the view of the session image may be adjusted so that the heart has a similar orientation and is at a similar cardiac-cycle event than the heart shown in the reference illustration 406 or in the reference image 407. The adjusting at 219 may be accomplished by least one of (a) adjusting an orientation of the probe (e.g., moving the probe) relative to the patient or (b) adjusting acquisition settings or parameters.

The workflow 200 includes acquiring at 220 ultrasound images of the anatomical structure. For example, after adjusting at least one of the orientation of the probe or the acquisition settings or parameters, the operator may activate a user-selectable element 414, which is indicated as a FREEZE button, to capture one or more ultrasound images. These ultrasound images may also be referred to as cardiac-cycle images (or captured images). In the illustrated embodiment, activation of the user-selectable element 414 may stop image recording and automatically save a predetermined number of image frames prior to activation of the user-selectable element 414. For example, the previous six or ten seconds of image frames may be saved. Accordingly, the acquired ultrasound image may include a series of image frames in which the anatomical structure in the image frames has a substantially common orientation.

Figure 4:
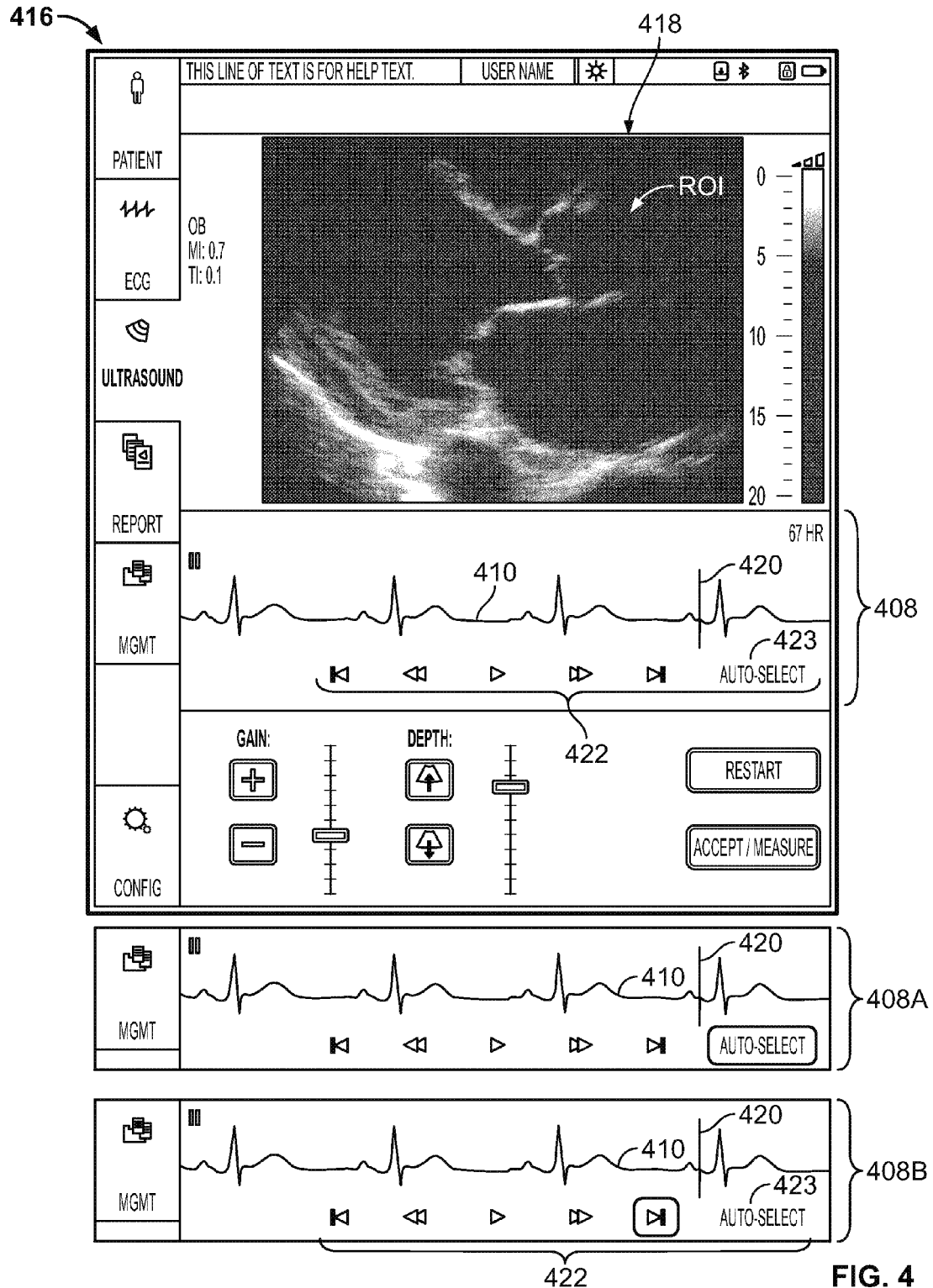
FIG. 4 shows another ultrasound-acquisition screen that may be displayed by the diagnostic ultrasound system of FIG. 1.

FIG. 4 shows another ultrasound-acquisition screen 416 that may be displayed to the operator. The ultrasound acquisition screen 416 may be similar to the ultrasound-acquisition screen 400, but the reference advisor 404 (FIG. 3) has been removed and the waveform portion 408 may be expanded. The ultrasound-acquisition screen 416 may be displayed when the user-selectable element 414 (FIG. 3) is activated by the operator. In FIG. 4, the signal waveform 410 shows the electrical activity of the patient's heart for four heartbeats.

The signal waveform 410 may be synchronized with the acquired ultrasound image. For example, FIG. 4 shows a single image frame 418 of a region of interest (ROI). The image frame 418 is from the acquired ultrasound image, which may include a series of image frames. In some embodiments, the ROI includes at least a portion of the heart. In particular embodiments, the image frame 418 includes a parasternal long-axis view of the left ventricle (LV). The image frame 418 directly corresponds to a designated time during acquisition of the ultrasound image. The designated time and, consequently, the image frame 418 directly corresponds to an electrical measurement along the signal waveform 410. In FIG. 4, a time indicator 420 is located at the designated time on the signal waveform 410. The time indicator 420 is illustrated as a vertical line and may have a color that differs from a color of the signal waveform. However, other GUI elements may be used to indicate time.

The workflow 200 may also include identifying at 222 an image frame from the acquired ultrasound image in order to obtain measurements. This image frame may also be referred to as a measurement frame. For example, when the ROI includes a heart, the measurement frame may show the heart at a predetermined moment or event during the cardiac cycle. To this end, when the user-selectable element 414 is activated, time-selection elements 422 may appear with the signal waveform 410. As shown in FIG. 4, the time-selection elements 422 include user-selectable elements. The time-selection elements 422 include an AUTO-SELECT element 423 that instructs the diagnostic system 100 to automatically identify an image frame that may be designated as the measurement frame or proposed to the operator as a potential measurement frame.

The automatic identification of an image frame may be performed in various manners. For example, the cardiac analyzer 124 may analyze the image frames of the recording and/or the signal waveform 410 to identify the image frame that is associated with a designated moment of the cardiac cycle. For instance, the cardiac analyzer 124 may analyze the anatomical structures shown in the image frames to identify when the anatomical structures have a predetermined relationship with respect to each other. More specifically, the cardiac analyzer 124 may analyze the movements of heart walls and valves and the change in chamber size to identify different stages in the heart cycle. In particular embodiments, the cardiac analyzer 124 identifies an ultrasound image that corresponds to an end diastole of the cardiac cycle.

After the cardiac analyzer 124 has automatically identified an image frame that is associated with a predetermined moment in the heart cycle, the operator may use the time-selection elements 422 to confirm or verify that the image frame identified by the cardiac analyzer 124 is the desired measurement frame. For example, the time-selection elements 422 also include virtual buttons that are similar to buttons of a video-cassette recorder (VCR) or DVD player. The time-selection elements 422 may enable the operator to forward, fast-forward, rewind, fast-rewind, and play the combined ultrasound/ECG recording. When the time indicator 420 is moved to a selected time, the image frame shown in the ultrasound-acquisition screen 416 is changed to the image frame that is associated with the selected time. Accordingly, the time-selection elements 422 may permit the operator to scan or move the time indicator 420 along the signal waveform 410 thereby changing the image frame to confirm/identify/select the measurement frame that is most representative of the predetermined moment in the heart cycle.

By way of example, the imaging device 108 may be capable of imaging at 50 frames/second. In such embodiments, each image frame 418 may correspond to 0.02 seconds. Accordingly, the time indicator 420 may be moved along the x-axis of the signal waveform 410 in incremental steps that correspond to 0.02 seconds. In some cases, the images frames before or after the image frame identified by the cardiac analyzer 124 may be a better representation of the predetermined moment in the cardiac cycle that is desired by the operator. The operator may then select the appropriate image frame by selecting the user-selectable element 422, which is a button that is labeled ACCEPT/MEASURE. In some cases, the appropriate image frame is the image frame that was automatically selected. The selected image frame is the measurement frame.

In the illustrated embodiment, the reference advisor 404 is removed when the ultrasound-acquisition screen 416 is shown. However, in other embodiments, the reference advisor 404 remains for the operator to compare a proposed image frame to the heart (or other anatomical object) that is shown in the reference illustration 406 or the reference image 407. As such, the operator may move amongst the image frames to select an image frame that is most similar to the reference illustration 406 or the reference image 407. In some embodiments, the reference image 407 is the measurement frame that was obtained during a previous imaging session.

Figure 5:
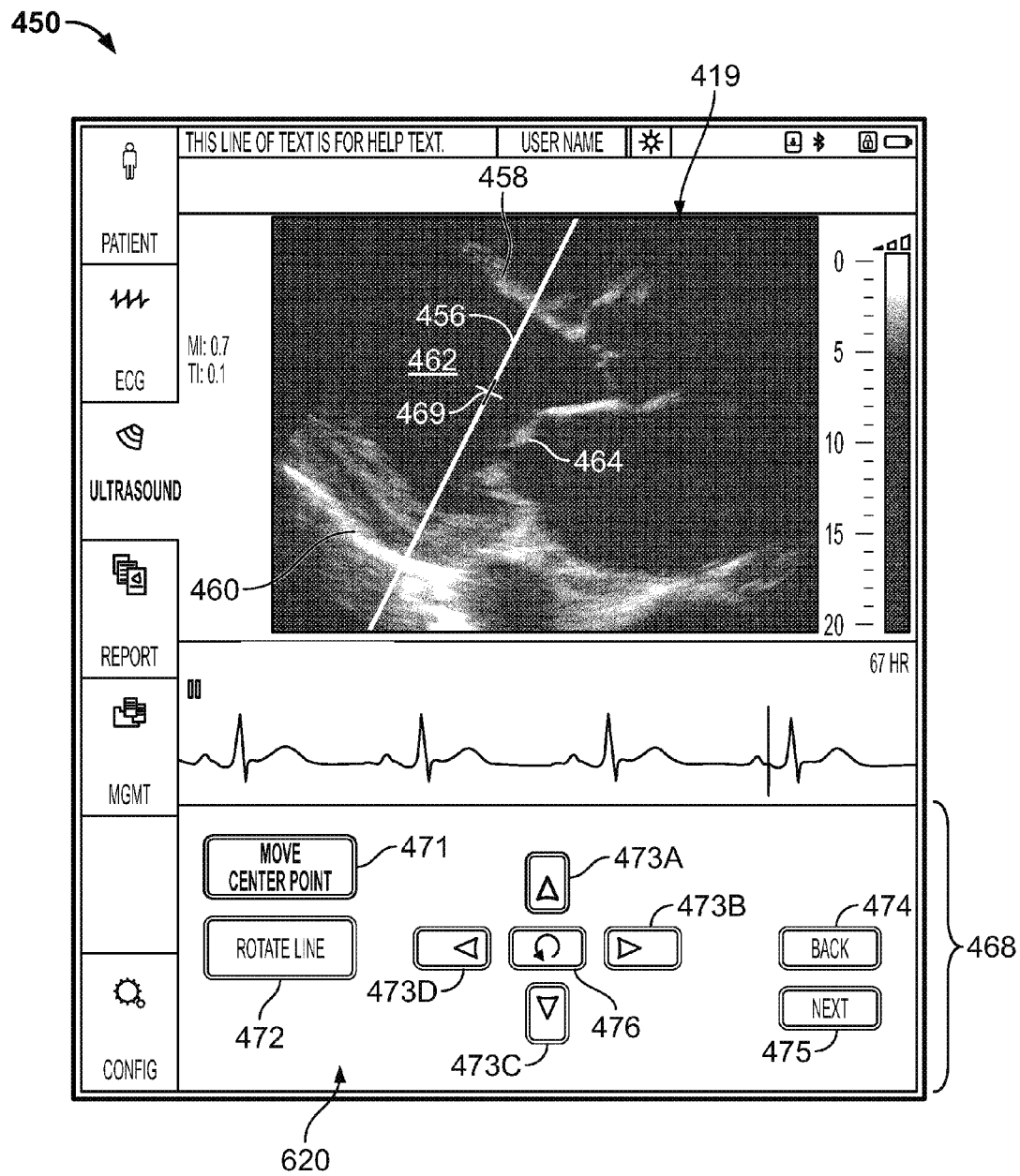
FIG. 5 shows a measurement screen that may be displayed by the diagnostic ultrasound system of FIG. 1.
Figure 6:
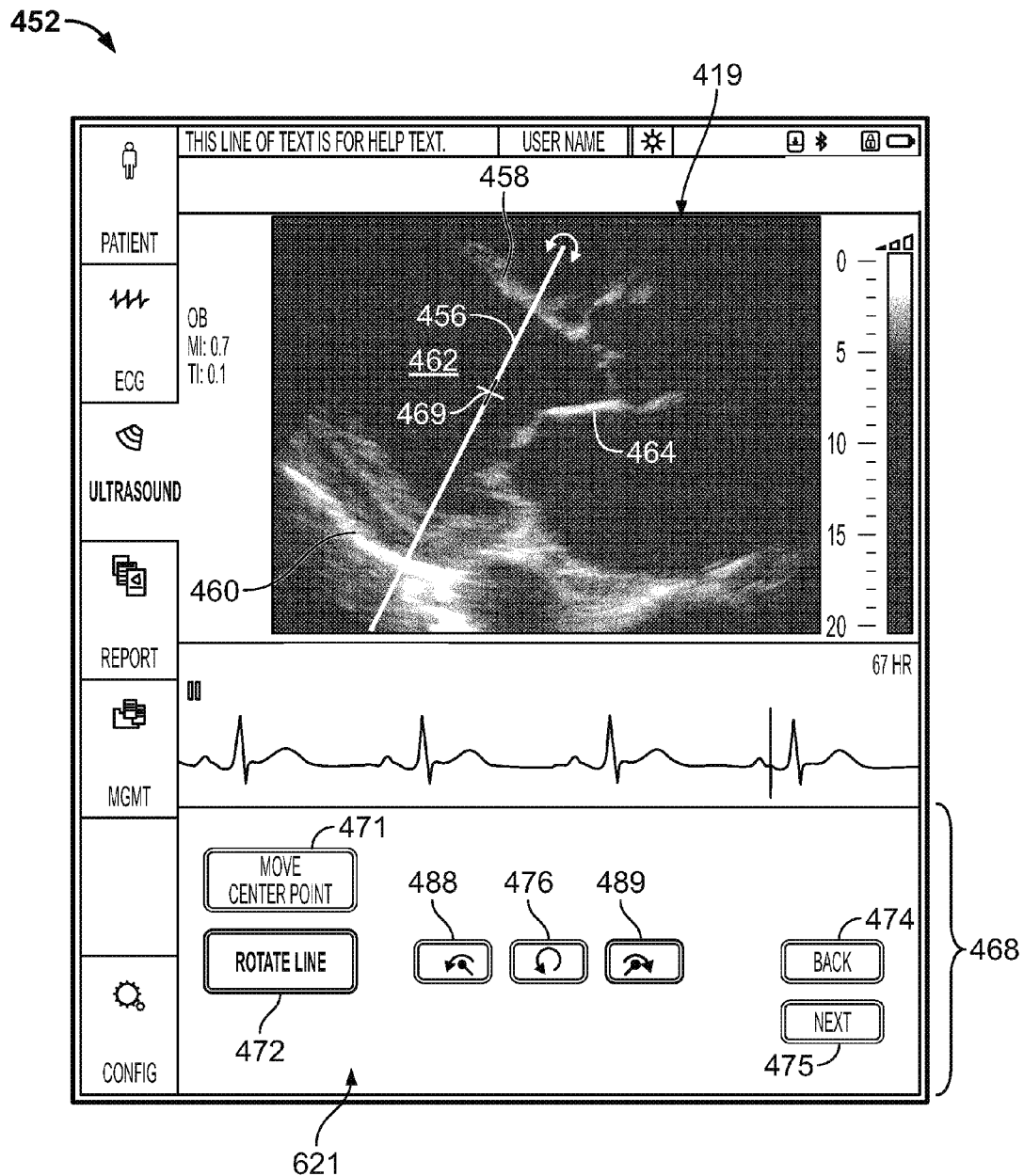
FIG. 6 shows another measurement screen that may be displayed by the diagnostic ultrasound system of FIG. 1.
Figure 7:
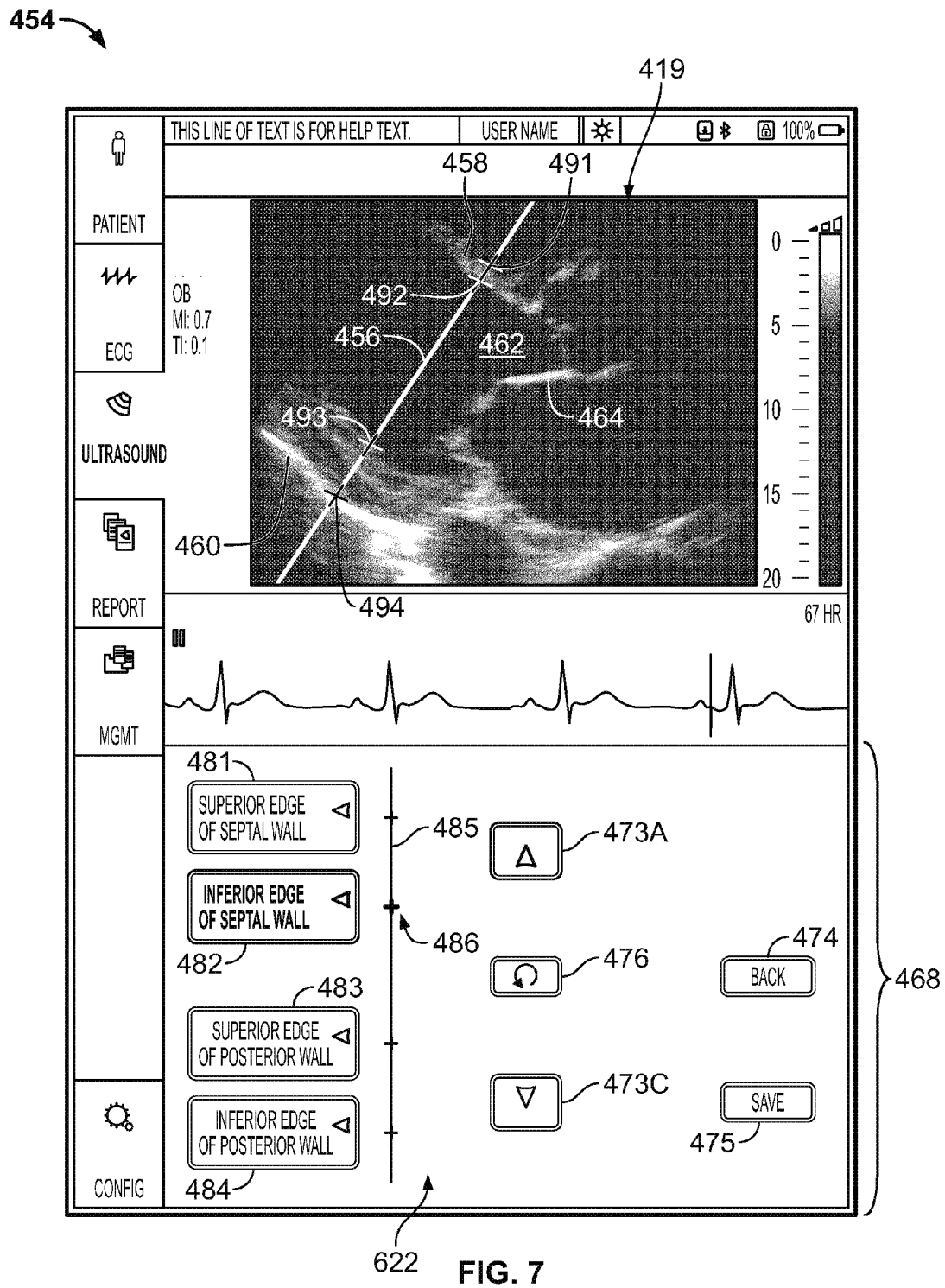
FIG. 7 shows another measurement screen that may be displayed by the diagnostic ultrasound system of FIG. 1.

FIGS. 5-7 illustrate respective measurement screens 450, 452, and 454 that may be shown to the operator during the measurement stage 266. The workflow 200 may include positioning at 224 a reference object 456 on a measurement frame 419 that was selected by the diagnostic system 100 and/or the operator as described above. As will be described in greater detail below, the reference object 456 may be used to obtain measurements (e.g., values of different dimensions) of anatomical structures 458, 460 shown in the measurement frame 419. In the illustrated embodiment, the reference object 456 is a projection line and, as such, may be referred to as the projection line 456 hereinafter. The illustrated anatomical structures 458, 460 include an inter-ventricular septal wall and a posterior wall, respectively, of the patient's heart and may also be referred to as the septal wall 458 and the posterior wall 460 hereinafter. Also shown in FIGS. 5-7, a chamber 462 is located between the septal and posterior walls 458, 460. A third anatomical structure 464, the atrioventricular (mitral)

valve (also referred to as a bicuspid valve), is also shown in FIGS. 5-7. The mitral valve 464 is located between the left ventricle and the left atrium.

The positioning operation 224 may include multiple stages or sub-operations for positioning the reference object 456. For example, with respect to FIG. 5, a first stage may include automatically positioning the reference object 456 with respect to the anatomical structures 458, 460. In the exemplary embodiment, the projection line 456 has a center point 469 that the projection line 456 is configured to be rotated about. The measurement module 125 may analyze the measurement frame 419 to identify one or more features of the heart shown in the measurement frame 419, such as at least one of the septal wall 458, the posterior wall 460, the chamber 462, or the mitral valve 464. The measurement module 125 may automatically position the center point 469 within the chamber 462 between the septal and posterior walls 458, 460 and proximate to the mitral valve 464. The measurement module 125 may also orient the projection line 456 such that the projection line 456 intersects the septal and posterior walls 458, 460 in a substantially perpendicular manner.

In FIG. 5, the user-selectable element 471 labeled MOVE CENTER POINT is indicated as being activated. The positioning operation 224 may also include receiving operator inputs to modify the position of the projection line 456. The measurement screen 450 includes a control portion 468 that includes user-selectable elements 471-476, which include center point locators 473A-473D. The center point locators 473A-473D are shown as four arrow keys (up, down, left, right) in FIG. 5 that, when activated, enable the operator to move the center point 469 of the projection line 456. When the center point 469 is moved, the remainder of the projection line 456 may follow the center point 469. The user-selectable element 476 is an "undo" feature that enables the operator to return to a previous setting, such as a previous position of the projection line 456 before the projection line was moved. Once the operator has confirmed that the position of the center point 469 is sufficient, the operator may activate the user-selectable element 475 labeled NEXT to transition to the measurement screen 452 shown in FIG. 6.

With respect to FIG. 6, the positioning operation 224 may also include receiving operator inputs to modify an orientation (or rotation) of the projection line 456. For example, the measurement screen 452 includes the control portion 468 that has user-selectable elements 488 and 489 in addition to the user-selectable elements 472, 474, 475, and 476. The user-selectable elements 488, 489 may be referred to as rotating elements that enable the operator to rotate the projection line 456 about the center point 469. The user-selectable element 488 allows the operator to rotate the projection line 456 in a counter-clockwise direction, and the user-selectable element 489 allows the operator to rotate the projection line 456 in a clockwise direction. Once the operator has confirmed that the rotation of the projection line 456 is sufficient, the operator may activate the user-selectable element 475 to transition to the measurement screen 454.

As described above, one or more embodiments described herein are configured to obtain one or more measurements (e.g., dimensions of anatomical structures, ECG recordings) from a patient. The obtained measurements may then be analyzed by the diagnostic system and/or a healthcare provider to diagnose a medical condition of the patient. To this end, the workflow 200 may also include positioning at 226 measurement markers 491-494 for measuring anatomical structures in the ultrasound image. In FIG. 7, the measurement screen 454 includes the control portion 468. The control portion 468 includes the user-selectable elements 473A, 473C, and 474-476. The control portion 468 also includes user-selectable elements 481-484. Similar to the object-positioning operation 224, the marker-positioning operation 226 may include multiple stages or sub-operations for locating the measurement markers 491-494.

For example, the marker-positioning operation 226 may include automatically locating the measurement markers 491-494 with respect to the anatomical structures 458, 460. In the illustrated embodiment, the measurement marker 491 is configured to be positioned on the superior edge of the septal wall 458; the measurement marker 492 is configured to be positioned on the inferior edge of the septal wall 458; the measurement marker 493 is configured to be positioned on the superior edge of the posterior wall 460; and the measurement marker 494 is configured to be positioned on the inferior edge of the posterior wall 460.

To automatically locate the measurement markers 491-494 on the measurement frame 419, the measurement module 125 may analyze the measurement frame 419 and, more particularly, the anatomical structures 458, 460 to determine where the superior and inferior edges of the septal wall 458 are located and where the superior and inferior edges of the posterior wall 460 are located. The measurement module 125 may use, for example, edge-detection algorithms and, optionally, stored data that may inform the measurement module 125 as to where the edges are typically located for a heart. For example, the measurement module 125 may analyze the pixel intensities of the pixels in the ultrasound image proximate to the areas where the projection line 456 intersects the septal and posterior walls 458, 460. After determining where the edges are located, the measurement module 125 may position the markers 491-494 at the respective locations.

However, in some embodiments, the diagnostic system 100 enables the operator to move the measurement markers 491-494 from the automatically determined locations. Accordingly, the marker-positioning operation 226 may include receiving operator inputs to move at least one of the measurement markers 491-494. In some embodiments, the markers 491-494 may be moved individually by the operator. For example, the user-selectable elements 481-484 (also called marker elements) are labeled, respectively, "Superior Edge of Septal Wall," "Inferior Edge of Septal Wall," "Superior Edge of Posterior Wall," and "Inferior Edge of Posterior Wall." If the operator desires to move any one of the measurement markers 491-494, the operator may activate the appropriate marker element and utilize the user-selectable elements 473A and 473C to move the corresponding marker along the projection line 456. For example, the user-selectable element 482 is indicated as being activated in FIG. 7. When the user-selectable element 482 is activated, the operator is enabled to move the measurement marker 492 along the projection line 456. In the illustrated embodiment, the measurement markers 491-494 are only moved along the projection line 456 (e.g., up or down the projection line 456) to the desired location. In other embodiments, the markers 491-494 are not limited to locations along the projection line 456.

To facilitate the operator in identifying the measurement marker that is being moved (also referred to as the "movable marker"), an appearance of the movable marker may be altered to indicate to the operator that the movable marker is capable of being moved by the user-selectable elements 473A and 473C. By way of example, in the illustrated embodiment, the user-selectable element 482 is activated. The measurement marker 492 is indicated in a different color as compared to when the user-selectable element 482 is not activated. For example, the measurement marker 492 may be pink or yellow, whereas the markers 491, 493, and 494 may be gray. The measurement marker 492 may also be gray when the user-selectable element 482 is not activated.

Moreover, the control portion 468 may include a representative line 485 having representative markers 486 located therealong. Each of the representative markers 486 is associated with a corresponding one of the user-selectable elements 481-484 and one of the measurement markers 491-494. The representative markers 486 may have a similar appearance (e.g., size, shape, and color) to the corresponding measurement markers 491-494. For example, when the user-selectable element 482 is activated as shown in FIG. 7, the representative marker 486 associated with the user-selectable element 482 and the measurement marker 492 may have a similar appearance. In the illustrated embodiment, the representative marker 486 associated with the user-selectable element 482 and the measurement marker 492 have the same size, shape, and color and are distinguishable from the other markers.

In some embodiments, the measurement markers 491-494 are configured to indicate a localized point within the measurement frame 419. As shown, the markers 491-494 are illustrated as cross-hairs. However, alternative markers may have alternative structures (e.g., size, shape, configurations) as well as other colors. For example, the markers may be dots, circles, triangles, arrows, and the like that indicate to the operator a particular location. In other embodiments, the markers 491-494 do not indicate a localized point but a larger area within the ultrasound image. For example, the markers 491-494 may be circles with a large diameter or circumference.

As shown by comparing FIGS. 5-7, the control portion 468 may change as the operator moves between the measurement screens 450, 452, and 454. The measurement screens 450, 452, 454 may have different arrangements of user-selectable elements to guide the operator during the measurement stage 266. In some cases, at least one of the user-selectable elements remains unchanged as the operator moves from one measurement screen to the next. For example, the measurement screen 450 has a first arrangement 620 that includes the user-selectable elements 471, 472, 473A-473D, and 474-476. The measurement screen 452 has a second arrangement 621 that includes the user-selectable elements 471, 472, 474, 475, and 476, which are shared by the first arrangement. However, the second arrangement 621 does not include some of the user-selectable elements in the first arrangement (e.g., the user-selectable elements 473A-473D). The second arrangement 621 also includes user-selectable elements 488 and 489. The third arrangement 622 of the control portion 468 is shown in FIG. 7 and includes the user-selectable elements 473A, 473C, 476, and 474. The third arrangement 622 does not include at least some of the user-selectable elements in the first and second arrangements. However, the third arrangement includes user-selectable elements 481-484.

Accordingly, when the operator moves from one measurement screen to the next, the arrangement of user-selectable elements may change. The change in the arrangement may facilitate guiding the operator by indicating to the operator what functionalities are available in the present measurement screen. By way of example, the first arrangement 620 in the measurement screen 450 indicates to the operator that the center point 469 may be moved in different x-y directions along the measurement frame 419. The second arrangement 621 in the measurement screen 452 indicates to the operator that the projection line 456 may be rotated about the center point 469. The third arrangement 622 indicates to the operator that the different markers 491-494 on the projection line 456 may be individually moved by the operator by activating one of the user-selectable elements 481-484. In such instances, the diagnostic system 100 provides a user-friendly interface that guides the operator along the various steps for determining different measurements.

The structural measurements may be calculated at 228. For example, the measurement module 125 may measure a distance between the markers 491 and 492. The measured distance may be representative of a septal wall thickness. The measurement module 125 may also measure a distance between the markers 493 and 494. The measured distance may be representative of a posterior wall thickness. In some embodiments, the measurement module 125 may also measure a distance between the markers 492 and 493, which may represent a chamber diameter. In some embodiments, the measurement module 125 may calculate other measurements based on the obtain measurements. For example, the measurement module 125 may calculate a LV mass.

After the workflow data is obtained (e.g., ECG and dimensions of anatomical structures), the workflow may also include generating at 230 a report. The report is based upon the obtained measurements and may simply provide those measurements. However, in other embodiments, the report may include a recommended diagnosis regarding a medical condition of interest. The report generator 126 may analyze various data, including the measurements, and determine whether the patient has a medical condition, such as LVH. For example, the measurements may include at least one of an LV mass, septal wall thickness, or posterior wall thickness. The ECG may include electrical abnormalities (e.g., in the PQRST waveform) that are indicative of the medical condition of interest. The report generator 126 may analyze at least one of the LV mass, the septal wall thickness, the posterior wall thickness, and/or the ECG to diagnose the medical condition of interest for the patient. For example if at least one of the LV mass, the septal wall thickness, or the posterior wall thicknesses exceed a designated value and/or if the ECG includes one or more abnormalities, the report generator 126 may generate a report that is indicative of a patient with the medical condition.

It should be noted that FIGS. 5-7 merely illustrate one example of embodiments described herein in which a heart is imaged and dimensions of the different structures in the heart are determined. However, other anatomical systems, organs, or structures of a patient body may be analyzed to determine measurements thereof. Moreover, in alternative embodiments, the reference object may have other geometric shapes that an operator may use as a reference or standard for obtaining measurements of anatomical structures.

Figure 8:
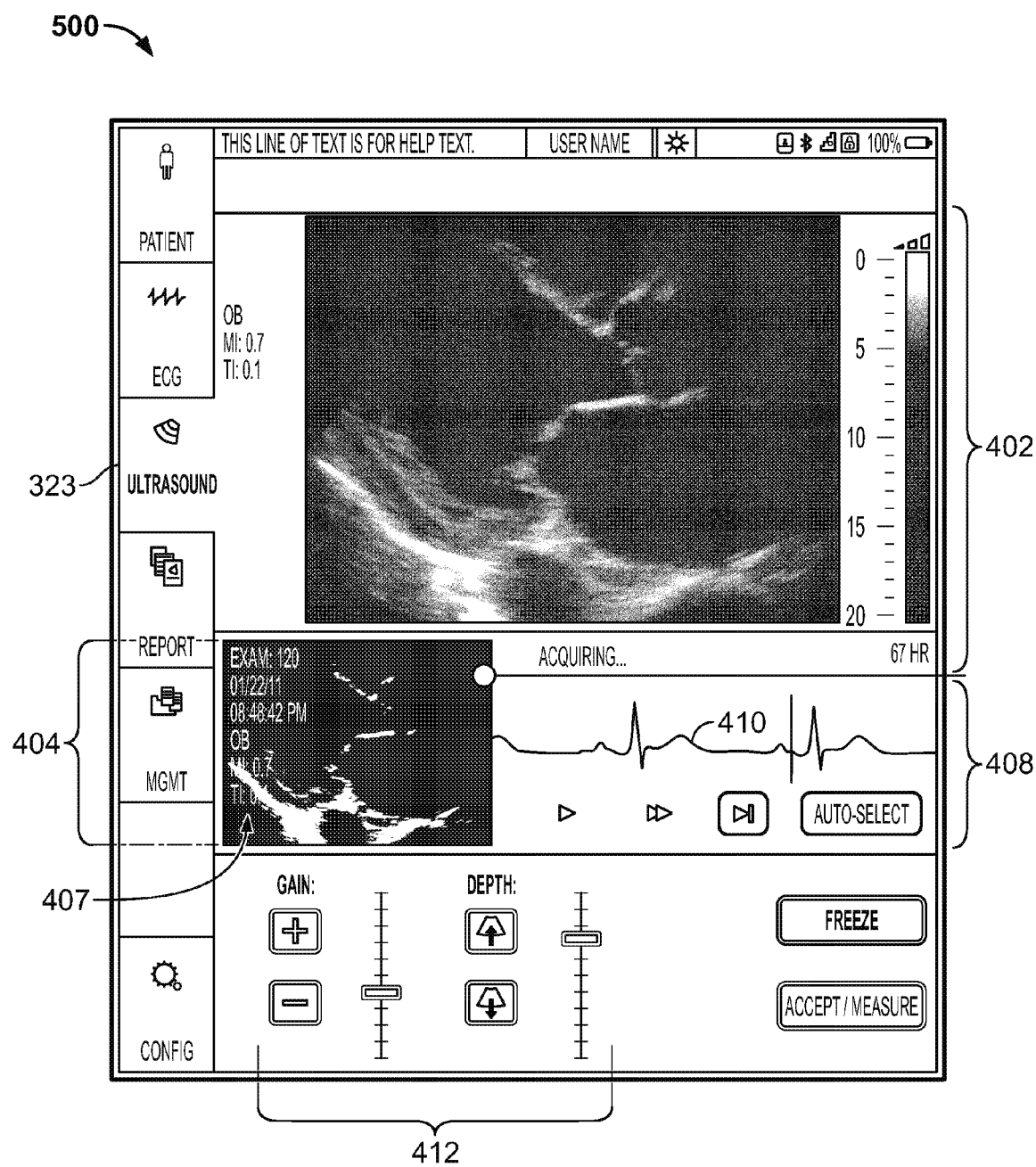
FIG. 8 shows another ultrasound-acquisition screen that may be displayed by the diagnostic ultrasound system of FIG. 1.

FIG. 8 shows another ultrasound-acquisition screen 500 that may be displayed to the operator when the ULTRASOUND tab 323 is activated (e.g., during the ultrasound-acquisition stage 264). The ultrasound-acquisition screen 500 is similar to the ultrasound-acquisition screen 400 shown in FIG. 3 above. For example, the ultrasound-acquisition screen 500 includes the image portion 402 where an ultrasound image is displayed and the reference advisor 404. The ultrasound-acquisition screen 500 may also include the waveform portion 408 in which the signal waveform 410 is displayed and the operator controls 412.

However, the reference advisor 404 does not include a reference illustration, such as the reference illustration 406 (FIG. 3). Instead, the reference advisor 404 includes the previously-acquired diagnostic ultrasound image 407. The previously-acquired ultrasound image 407 may have been acquired during a prior imaging session (e.g., a first imaging session). The ultrasound image 407 may be the measurement frame that was selected as described above with respect to the measurement frame 419. In other embodiments, the ultrasound image 407 is a series of image frames. For example, the ultrasound image 407 may be repeatedly played as a cine movie when the ultrasound-acquisition screen 500 is shown. As such, during a second imaging session that occurs after the first imaging session, the diagnostic system 100 may show the operator the measurement frame 419.

Figure 9:
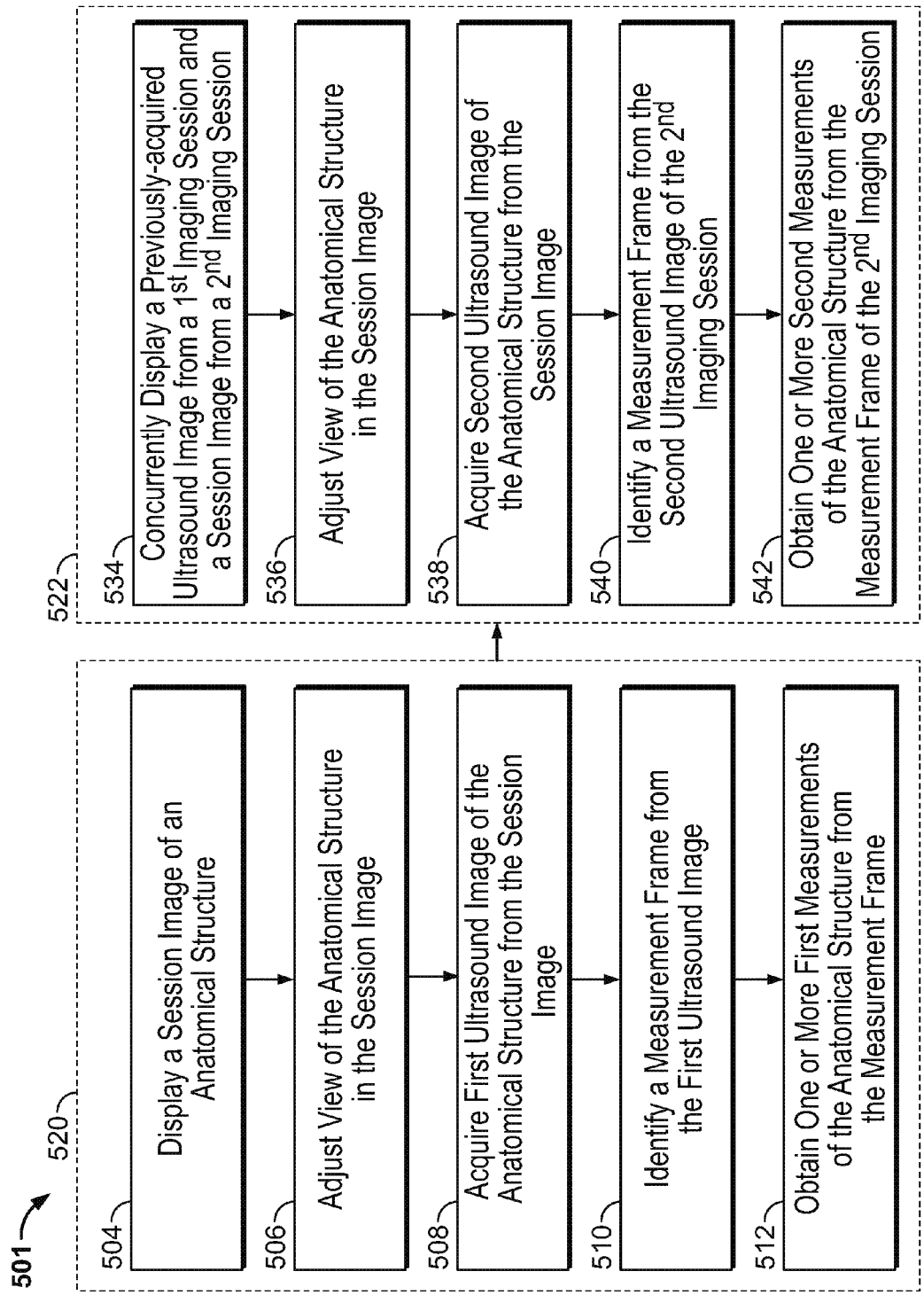
FIG. 9 is a flow chart that illustrates a method of obtaining measurements of an anatomical structure in accordance with one embodiment.

FIG. 9 is a flow chart that illustrates a method 501 of obtaining measurements of an anatomical structure. The method 501 may be performed during separate first and second imaging sessions 520, 522. In some embodiments, the first imaging session 520 provides baseline data of the anatomical structure and the second imaging session provides data about the anatomical structure after a therapy and/or stimulus has been applied to the anatomical structure.

The method 501 includes displaying at 504 an ultrasound image of an anatomical structure to an operator. In order to distinguish the ultrasound image from other ultrasound images described herein, the ultrasound image that is displayed at 504 may also be referred to as a session image. The session image may be a single ultrasound image frame or a set of image frames (e.g., a series of frames). In some embodiments, the session image is a real-time image of the anatomical structure. For example, the operator may control an ultrasound probe and utilize the ultrasound probe to adjust a view of the session image in real-time on an operator display. In other embodiments, the session image is not a real-time image. For example, the session image may be processed from 3D ultrasound data that was previously acquired. The operator may select different views of the anatomical structure by manipulation of the 3D ultrasound data.

The method 501 includes adjusting at 506 the view of the anatomical structure in the session image so that the anatomical structure has a designated orientation. The designated orientation may be relative to the probe or one or more landmark(s) within the patient body. The method 501 also includes acquiring at 508 a first ultrasound image of the anatomical structure from the session image. The first ultrasound image includes the anatomical structure at the designated orientation. The First ultrasound image may also include the anatomical structure in a designated condition or state. For example, when the anatomical structure is a heart, the event may be a predetermined cardiac-cycle event.

At 510, a measurement frame from the first ultrasound image may be identified. The first ultrasound image may include a series of ultrasound image frames. The measurement frame may be automatically identified by a diagnostic system as described above and/or the diagnostic system may enable the operator to identify a measurement frame. In particular embodiments, the measurement frame includes the anatomical structure at the designated condition or state. For example, the heart may be at an end diastole event of the cardiac cycle. However, the heart may be at other events of the cardiac cycle, such as early diastole, mid-diastole, early systole, mid-systole, or end systole. In each of the above events, the different cardiac structures (e.g., walls, valves, groups of cardiac cells) may have a relative position with respect to one another. A cardiac event may also be other conditions of the heart, such as when an aortic pressure is greatest, the ventricular volume is least, or when the R-point of the PQRST waveform in an ECG exists.

One or more measurements of the anatomical structure in the measurement frame may be obtained at 512. The measurements may be any measurements that may be determined from an ultrasound image of the anatomical structure. The measurements may include dimensions (e.g., thickness or separation distance between two structures), volume, area, and the like. The obtaining at 512 may include positioning operations 224, 226 (FIG. 3). The positioning operations 224, 226 may include one or more sub-stages as described above. The obtaining operation 512 may also include the calculating operation 228 described above.

During the second imaging session 522, an ultrasound image (or session image) from the second imaging session 522 may be displayed at 534 to an operator. The displaying operation 534 may include concurrently displaying a previously-acquired ultrasound image from the first imaging session 520 in addition to the session image of the second imaging session 522. Simultaneous displaying may include showing the previously-acquired ultrasound image and the session image side-by-side on a single display or multiple displays. For example, a first display may present the previously-acquired image to the operator, and second display may present the session image to the operator. In particular embodiments, the previously-acquired image is the measurement frame from the first imaging session 520.

As another example, simultaneous displaying may include showing the previously-acquired image and the session image in an overlapping manner where at least one of the previously-acquired image and the session image is at least partially transparent. The previously-acquired image and the session image may also have different colors. As such, the overlapping display may assist a user in orienting the probe so that the anatomical structure in the session image substantially coincides with the anatomical structure in the previously-acquired image.

During the second imaging session 522, the view of the anatomical structure in the session image may be adjusted at 536. The previously-acquired image of the anatomical structure may assist the operator in adjusting the probe and/or the settings or parameters of the diagnostic system so that the view of the anatomical structure in the session image is substantially similar to the view of the anatomical structure that was captured in the first ultrasound imaging session.

At 538, a second ultrasound image of the anatomical structure may be acquired. The anatomical structure in the second ultrasound image may have a similar orientation and have a similar condition or state as the anatomical structure in the first ultrasound image. For example, when the anatomical structure is a heart, the condition or state may be a predetermined cardiac-cycle event.

A measurement frame may be identified at 540 from the second ultrasound image. The identification may be automatically performed by the diagnostic system as described above. In some embodiments, an algorithm for automatically identifying the measurement frame may include using data derived from the first ultrasound image. For instance, the algorithm may determine the relative positions of the different parts of the anatomical structure and analyze the second ultrasound image to identify a measurement frame that has the different parts of the anatomical structure in similar relative positions. The algorithm may also use the electrical activity data to identify the measurement frame.

The method 501 may also include obtaining at 542 one or more second measurements of the anatomical structure from the identified measurement frame of the second imaging session. In some embodiments, the method 501 may include generating a report that includes the first and second measurements that were obtained. The report may also provide one or more relevant statistics or values that may assist a healthcare provider in diagnosing a medical condition of the anatomical structure.

Figure 10:
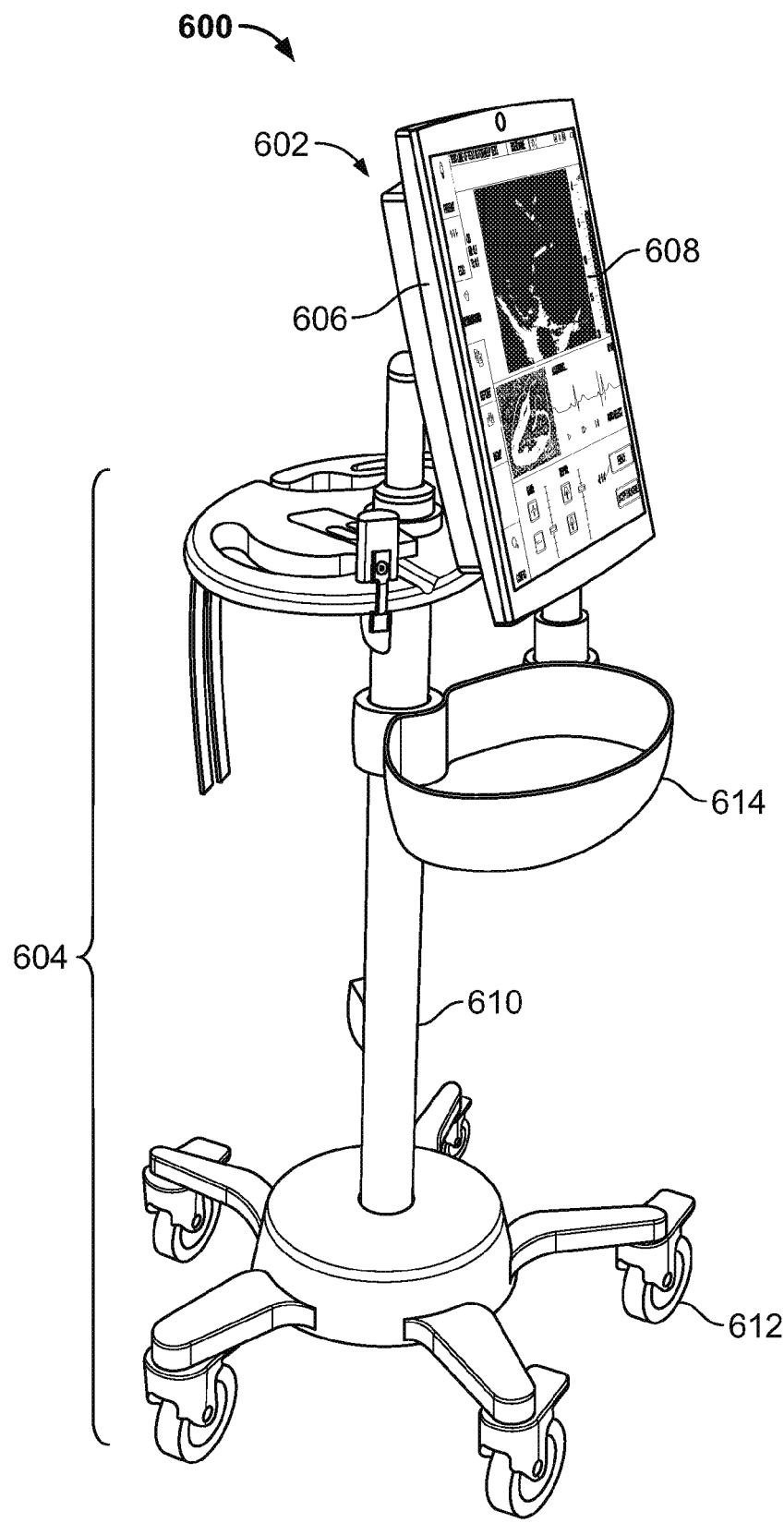
FIG. 10 is a perspective view of a portable diagnostic ultrasound system formed in accordance with one embodiment.

FIG. 10 is a perspective view of a portable diagnostic system 600 formed in accordance with one embodiment. The diagnostic system 600 may be similar to the diagnostic system 100 (FIG. 1) and include similar features. In the illustrated embodiment, the diagnostic system 600 includes a workstation or console 602 and a movable carrier 604 that supports the workstation 602. The workstation 602 is configured to be communicatively coupled to an ultrasound probe (not shown) and/or one or more electrodes (not shown) configured to obtain electrical data from a patient. The workstation 602 includes a system body or housing 606 that holds a computing system (not shown) and base units (not shown) of an ECG device and an ultrasound imaging device. The computing system and base units may be similar to the computing system 102 and the base units 112, 116 shown in FIG. 1. The workstation 602 also includes a display 608 that may be part of a user interface of the diagnostic system 600. The display 608 is a touch-sensitive display in one embodiment and may operate in a similar manner as the display 110 described above. As shown, the diagnostic system 600 enables an individual (e.g., the operator) to move the workstation 602 using the carrier 604. The carrier 604 may include a post or stand 610 and a plurality of wheels 612 for moving the workstation 602. The carrier 604 may also include a basket 614 for holding various components, such as the probe and the leads.

A technical effect of the various embodiments of the systems and methods described herein include user-friendly interfaces for obtaining structural measurements of an anatomical structure(s) in a patient body. The user interface may also direct or guide the operator throughout a workflow to obtain the desired data (e.g., electrical and ultrasound data). Another technical effect may be to direct or guide the operator to obtain comparable measurements from different imaging sessions. Another technical effect may be the generation of a report that assists a qualified individual (e.g., doctor) in diagnosing a cardiac medical condition (e.g., LVH) of a patient. Other technical effects may be provided by the embodiments described herein.

As described above, the various components and modules described herein may be implemented as part of one or more computers or processors. The computer or processor may include a microprocessor. The microprocessor may be connected to a communication bus. The computer or processor may also include a memory. The memory may include Random Access Memory (RAM) and Read Only Memory (ROM). The computer or processor further may include a storage system or device, which may be a hard disk drive or a removable storage drive such as a floppy disk drive, optical disk drive, and the like. The storage system may also be other similar means for loading computer programs or other instructions into the computer or processor. The instructions may be stored on a tangible and/or non-transitory computer readable storage medium coupled to one or more servers.

As used herein, the term "computer" or "computing system" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "computing system."

The set of instructions may include various commands that instruct the computer or processor as a processing machine to perform specific operations such as the methods and processes described herein. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine. The program is complied to run on both 32-bit and 64-bit operating systems. A 32-bit operating system like Windows XP™ can only use up to 3 GB bytes of memory, while a 64-bit operating system like Window's Vista™ can use as many as 16 exabytes (16 billion GB).

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Thus, in one embodiment, an ultrasound diagnostic system is provided that includes a storage system configured to store a reference image frame of a heart. The reference image frame is acquired during a first ultrasound imaging session. The reference image frame includes the heart at a corresponding orientation and at a corresponding cardiac condition. The diagnostic system also includes an ultrasound imaging device having an ultrasound probe that is configured to provide an ultrasound image of the heart during a second ultrasound imaging session. The diagnostic system also includes a user interface including an operator display that is configured to concurrently display the reference image frame and the ultrasound image of the second ultrasound imaging session. The user interface is configured to receive operator inputs to adjust a view of the heart in the second ultrasound image and acquire a set of image frames of the heart. The diagnostic system also includes a cardiac analyzer that is configured to automatically identify a measurement frame from the set of image frames. The measurement frame includes the heart at a designated orientation that is similar to the corresponding orientation of the reference image frame and includes the heart at a designated cardiac condition that is similar to the cardiac condition of the reference image frame.

In one aspect, the operator inputs include at least one of moving the probe or changing acquisition parameters of the imaging device.

In another aspect, the reference image frame and the measurement frame are of a common ultrasound image modality.

In another aspect, the ultrasound diagnostic system is a portable diagnostic system.

In another aspect, the designated cardiac condition is a predetermined cardiac-cycle event. For example, the predetermined cardiac-cycle event may be an end diastole of a cardiac cycle.

In another aspect, the diagnostic system includes a report generator that is configured to generate a report that includes a first measurement of the heart that is obtained from the reference image and a comparable second measurement of the heart that is obtained from the measurement frame. The first and second measurements may be of a common cardiac structure when the heart is at a substantially common contractive state.

In another embodiment, an ultrasound diagnostic is provided that includes a storage system configured to store a previously-acquired reference image of a heart. The reference image is from a first ultrasound imaging session and includes the heart at a corresponding orientation. The diagnostic system also includes an ultrasound imaging device having an ultrasound probe that is configured to acquire a real-time image of the heart during a second ultrasound imaging session. The probe is configured to be controlled by an operator to change a view of the heart. The diagnostic system also includes a user interface having an operator display that is configured to concurrently display to the operator the reference and real-time images during the second imaging session. The user interface is configured to receive operator inputs to acquire a cardiac-cycle image of the heart from the real-time image. The diagnostic system also includes a cardiac analyzer that is configured to automatically identify a measurement frame from the cardiac-cycle image. The measurement frame includes the heart at a designated orientation that is similar to the corresponding orientation of the reference image frame and includes the heart at a designated cardiac condition.

In one aspect, the reference image is a single image frame that was used to obtain measurements of the heart. The heart may be at a corresponding cardiac condition in the single image frame that is similar to the designated cardiac condition of the measurement frame.

In another aspect, the designated cardiac condition is a predetermined cardiac-cycle event. The predetermined cardiac-cycle event may be an end diastole of a cardiac cycle.

In another aspect, the diagnostic system also includes a report generator that is configured to generate a report that includes a first measurement of the heart that is obtained from the reference image and a comparable second measurement of the heart that is obtained from the measurement frame. The first and second measurements may be of a common cardiac structure when the heart is at a substantially common contractive state.

In another embodiment, a method of obtaining ultrasound images of a heart is provided. The method includes displaying a reference image acquired from a first ultrasound imaging session. The reference image includes the heart at a corresponding orientation. The reference image is displayed during a second ultrasound imaging session that occurs after the first ultrasound imaging session. The method also includes displaying a real-time image of the heart that is obtained by an ultrasound probe during the second imaging session. The real-time image and the reference image are displayed concurrently to an operator. The method also includes adjusting a view of the heart in the real-time image and acquiring a cardiac-cycle image of the heart from the real-time image. The cardiac-cycle image includes the heart at a designated orientation that is similar to the corresponding orientation of the heart in the reference image. The method also includes automatically identifying a measurement frame from the cardiac-cycle image. The measurement frame includes the heart at the designated orientation and includes the heart at a designated cardiac condition.

In one aspect, the reference image is a single image frame that was used to obtain measurements of the heart. The heart is at a corresponding cardiac condition in the single image frame that is similar to the designated cardiac condition of the measurement frame.

In another aspect, the method includes obtaining measurements of the heart in the measurement frame.

In another aspect, the method includes obtaining a first measurement of the heart from the reference image and obtaining a comparable second measurement of the heart from the measurement frame. The method may also include generating a report that has the first and second measurements.

In one embodiment, a medical diagnostic system is provided that includes an electrocardiograph (ECG) device having electrodes that are configured to obtain electrical data for a heart. The diagnostic system also includes an ultrasound imaging device having an ultrasound probe that is configured to obtain ultrasound data of the heart. The diagnostic system also includes a user interface having a display. The user interface is configured to receive operator inputs from an operator of the diagnostic system, wherein the user interface is configured to show on the display a plurality of different screens to the operator during a workflow. The screens include user-selectable elements that are configured to be activated by the operator during the workflow. The user interface is configured to display the different screens to guide the operator through the workflow to obtain the electrical data and the ultrasound data. The user interface also configured to guide the operator to obtain structural measurements of the heart based on the ultrasound data.

In one embodiment, a medical diagnostic system is provided that includes an ultrasound imaging device having an ultrasound probe that is configured to obtain ultrasound data of a heart. The diagnostic system also includes a cardiac analyzer that is configured to analyze the ultrasound data to automatically identify a cardiac-cycle image from a set of ultrasound images based on the ultrasound data. The cardiac-cycle image includes the heart at a predetermined cardiac-cycle event. The diagnostic system also includes a measurement module that is configured to analyze the cardiac-cycle image and automatically position a reference object relative to at least one anatomical structure of the heart in the cardiac-cycle image. The diagnostic system also includes a user interface having a display configured to display the reference object and the cardiac-cycle image. The user interface is configured to receive operator inputs to at least one of (a) designate, from the set of ultrasound images, a different ultrasound image as the cardiac-cycle image or (b) re-position the reference object relative to the at least one anatomical structure.

In another embodiment, a method of obtaining measurements of a heart is provided. The method includes automatically identifying a cardiac-cycle image from a set of ultrasound images. The cardiac-cycle image includes the heart at a predetermined cardiac-cycle event. The method also includes displaying the cardiac-cycle image to an operator using a user interface display. The method also includes automatically positioning a reference object relative to at least one anatomical structure of the heart in the cardiac-cycle image. The reference object is positioned to obtain designated measurements of the heart. The method also includes receiving operator inputs from the operator to at least one of (a) designate, from the set of ultrasound images, a different ultrasound image as the cardiac-cycle image or (b) re-position the reference object relative to the at least one anatomical structure. The method also includes determining at least one measurement of the heart using the reference object and the cardiac-cycle image.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An ultrasound diagnostic system comprising:
   a storage system configured to store a reference image frame of a heart, the reference image frame being acquired during a first ultrasound imaging session, the reference image frame including the heart at a corresponding orientation and at a corresponding cardiac condition;
   an ultrasound imaging device including an ultrasound probe that is configured to provide an ultrasound image of the heart during a second ultrasound imaging session;
   a user interface comprising an operator display configured to concurrently display the reference image frame and the ultrasound image of the second ultrasound imaging session, the user interface configured to receive operator inputs to adjust a view of the heart in the ultrasound image and acquire a set of image frames of the heart; and
   a cardiac analyzer configured to automatically identify a measurement frame from the set of image frames, the measurement frame including the heart at a designated orientation that is similar to the corresponding orientation of the reference image frame and including the heart at a designated cardiac condition that is similar to the cardiac condition of the reference image frame;
   wherein the user interface is configured to display time-selection elements on the operator display after the measurement frame is automatically identified by the cardiac analyzer, the time-selection elements configured to be activated by a user to view the other image frames of the set of image frames on the operator display and select a different measurement frame from the set of image frames.

2. The ultrasound diagnostic system of claim 1, wherein the operator inputs include at least one of moving the probe or changing acquisition parameters of the imaging device.

3. The ultrasound diagnostic system of claim 1, wherein the reference image frame and the measurement frame are of a common ultrasound image modality.

4. The ultrasound diagnostic system of claim 1, wherein the ultrasound diagnostic system is a portable diagnostic system.

5. The system of claim 1, wherein the designated cardiac condition is a predetermined cardiac-cycle event.

6. The system of claim 1, further comprising a report generator configured to generate a report that includes a first measurement of the heart that is obtained from the reference image and a comparable second measurement of the heart that is obtained from the different measurement frame selected by the user, wherein the first and second measurements are of a common cardiac structure when the heart is at a substantially common contractive state.

7. The system of claim 1, wherein the user interface is configured to receive the operator inputs to adjust the view of the ultrasound image while the reference image is displayed to the user and as the ultrasound image is obtained through the ultrasound probe.

8. The system of claim 1, wherein a measurement screen is displayed on the operator display after the different measurement frame is selected by the user, the measurement screen including the different measurement frame, a reference object, and user-selectable elements that are configured to be activated by the user to move the reference object.

9. An ultrasound diagnostic system comprising:
   a storage system configured to store a previously-acquired reference image of a heart, the reference image being from a first ultrasound imaging session, the reference image including the heart at a corresponding orientation;
   an ultrasound imaging device including an ultrasound probe that is configured to acquire a real-time image of the heart during a second ultrasound imaging session, the probe configured to be controlled by a user to change a view of the heart;
   a user interface comprising an operator display configured to concurrently display to the user the reference and real-time images during the second imaging session user in acquiring a cardiac-cycle image of the heart, the user interface configured to receive operator inputs to adjust a view of the real-time image while the reference image is displayed to the user and receive operator inputs to acquire the cardiac-cycle image of the heart from the real-time image; and
   a cardiac analyzer configured to automatically identify a measurement frame from the cardiac-cycle image, the measurement frame including the heart at a designated orientation that is similar to the corresponding orientation of the reference image frame and including the heart at a designated cardiac condition.

10. The system of claim 9, wherein the reference image is a single image frame that was used to obtain measurements of the heart, the heart being at a corresponding cardiac condition in the single image frame that is similar to the designated cardiac condition of the measurement frame.

11. The system of claim 9, wherein the designated cardiac condition is a predetermined cardiac-cycle event.

12. The system of claim 11, wherein the predetermined cardiac-cycle event is an end diastole of a cardiac cycle.

13. The system of claim 9, further comprising a report generator configured to generate a report that includes a first measurement of the heart that is obtained from the reference image and a comparable second measurement of the heart that is obtained from the cardiac-cycle image, wherein the first and second measurements are of a common cardiac structure when the heart is at a substantially common contractive state.

14. The system of claim 9, wherein the cardiac-cycle image includes a set of image frames and the user interface is configured to display time-selection elements on the operator display after the measurement frame is automatically identified by the cardiac analyzer, the time-selection elements configured to be activated by a user to view the other image frames of the set of image frames on the operator display and select a different measurement frame from the set of image frames.

15. The system of claim 9, further comprising a workflow module, the workflow module configured to display first and second screens on the operator display to guide the user in obtaining a measurement of the heart after the measurement frame is identified, each of the first and second screens including the measurement frame, a reference object, and user-selectable elements that are configured to be activated by the user to move the reference object, the second screen being displayed on the operator display after the first screen.

16. A method of obtaining an ultrasound image frame, the method comprising:
- displaying a reference image acquired from a first ultrasound imaging session, the reference image including the heart at a corresponding orientation, the reference image being displayed during a second ultrasound imaging session that occurs after the first ultrasound imaging session;
- displaying a real-time image of the heart that is obtained by an ultrasound probe during the second imaging session, the real-time image and the reference image being displayed concurrently to a user;
- receiving operator inputs to adjust a view of the heart in the real-time image while the reference image is displayed; and
- receiving operator inputs to acquire a cardiac-cycle image of the heart from the real-time image, the cardiac-cycle image including the heart at a designated orientation that is similar to the corresponding orientation of the heart in the reference image;
- automatically identifying a measurement frame from the cardiac-cycle image, the measurement frame including the heart at the designated orientation and including the heart at a designated cardiac condition.

17. The method of claim 16, wherein the reference image is a single image frame that was used to obtain measurements of the heart, the heart being at a corresponding cardiac condition in the single image frame that is similar to the designated cardiac condition of the measurement frame.

18. The method of claim 16, wherein the designated cardiac condition is a an end diastole of a cardiac cycle.

19. The method of claim 16, further comprising obtaining measurements of the heart in the measurement frame.

20. The method of claim 16, further comprising obtaining a first measurement of the heart from the reference image and obtaining a comparable second measurement of the heart from the measurement frame, the method further comprising generating a report that includes the first and second measurements.

* * * * *